(12) United States Patent
Onoue et al.

(10) Patent No.: US 10,772,836 B2
(45) Date of Patent: Sep. 15, 2020

(54) METHOD FOR PRODUCING PARTICLES

(71) Applicants: RICOH COMPANY, LTD., Tokyo (JP); SHIZUOKA PREFECTURAL UNIVERSITY CORPORATION, Shizuoka (JP)

(72) Inventors: Satomi Onoue, Shizuoka (JP); Hideyuki Sato, Shizuoka (JP); Yoshiki Seto, Shizuoka (JP); Tatsuru Moritani, Shizuoka (JP); Tadahiko Morinaga, Shizuoka (JP)

(73) Assignees: RICOH COMPANY, LTD., Tokyo (JP); SHIZUOKA PREFECTURAL UNIVERSITY CORPORATION, Shizuoka (JP)

( * ) Notice: Subject to any disclaimer, the term of this patent is extended or adjusted under 35 U.S.C. 154(b) by 0 days.

(21) Appl. No.: 16/081,512

(22) PCT Filed: Mar. 2, 2017

(86) PCT No.: PCT/JP2017/008384
§ 371 (c)(1),
(2) Date: Aug. 31, 2018

(87) PCT Pub. No.: WO2017/150692
PCT Pub. Date: Sep. 8, 2017

(65) Prior Publication Data
US 2019/0076361 A1 Mar. 14, 2019

(30) Foreign Application Priority Data

Mar. 4, 2016 (JP) .................................. 2016-042424
Feb. 28, 2017 (JP) .................................. 2017-036690

(51) Int. Cl.
*A61K 9/16* (2006.01)
*B01J 2/18* (2006.01)
(Continued)

(52) U.S. Cl.
CPC .......... *A61K 9/1682* (2013.01); *A61K 9/5089* (2013.01); *A61K 9/5161* (2013.01);
(Continued)

(58) Field of Classification Search
CPC .. C03G 9/08; G03G 9/08757; G03G 9/08755; G03G 9/0802
See application file for complete search history.

(56) References Cited

U.S. PATENT DOCUMENTS

2007/0114306 A1  5/2007  Kawakami et al.
2008/0257021 A1  10/2008  Gruell et al.
(Continued)

FOREIGN PATENT DOCUMENTS

EP    2653217 A1    10/2013
JP    2008-100997   5/2008
(Continued)

OTHER PUBLICATIONS

A Kulikowska, I Wasiak, T Ciach. "Synthesis of carboxymethylcellulose nanoparticles using various coiling agents." Inzynieria I Aparatura Chemiczna, vol. 53, No. 4, 2014, pp. 268-269. (Year: 2014).*
(Continued)

*Primary Examiner* — Isaac Shomer
(74) *Attorney, Agent, or Firm* — Oblon, McClelland, Maier & Neustadt, L.L.P.

(57) ABSTRACT

A method for producing particles, the method including: applying vibration to a liquid including a physiologically active substance and included in a liquid-column resonance liquid-chamber to form a standing wave based on liquid column resonance, to thereby discharge the liquid from at least one discharging port, which is formed in an amplitude direction of the standing wave, to at least one region
(Continued)

corresponding to at least one anti-node of the standing wave; and drying the liquid discharged, to thereby form particles.

17 Claims, 11 Drawing Sheets

(51) Int. Cl.
*A61K 9/51* (2006.01)
*A61K 9/50* (2006.01)
*B01J 2/04* (2006.01)
*B29B 9/12* (2006.01)
*B29B 9/10* (2006.01)

(52) U.S. Cl.
CPC . *B01J 2/04* (2013.01); *B01J 2/18* (2013.01); *B29B 9/10* (2013.01); *B29B 9/12* (2013.01); *B29B 2009/125* (2013.01)

(56) References Cited

U.S. PATENT DOCUMENTS

| | | | |
|---|---|---|---|
| 2009/0042122 A1* | 2/2009 | Guay | G03G 9/0827 430/111.4 |
| 2009/0053174 A1 | 2/2009 | Kaneko et al. | |
| 2009/0317735 A1 | 12/2009 | Ohtani et al. | |
| 2010/0029667 A1 | 2/2010 | Ketner et al. | |
| 2010/0104970 A1 | 4/2010 | Norikane et al. | |
| 2011/0003695 A1* | 1/2011 | Asakawa | A61K 8/062 504/300 |
| 2012/0094231 A1* | 4/2012 | Norikane | B01J 2/04 430/137.1 |
| 2012/0270147 A1 | 10/2012 | Katoh et al. | |
| 2013/0069263 A1* | 3/2013 | Katoh | G03G 9/0802 264/9 |
| 2013/0273188 A1 | 10/2013 | Takahashi et al. | |
| 2013/0309497 A1* | 11/2013 | Takezaki | C08J 3/14 428/402 |
| 2014/0038100 A1* | 2/2014 | Katoh | G03G 9/0802 430/137.1 |
| 2014/0242514 A1* | 8/2014 | Inoue | G03G 9/0804 430/137.22 |
| 2014/0272695 A1 | 9/2014 | Moritani et al. | |
| 2016/0147167 A1 | 5/2016 | Moritani et al. | |

FOREIGN PATENT DOCUMENTS

| | | |
|---|---|---|
| JP | 2008-276146 | 11/2008 |
| JP | 2008-292976 | 12/2008 |
| JP | 4293572 | 4/2009 |
| JP | 2009-519812 | 5/2009 |
| JP | 2010-102195 | 5/2010 |
| JP | 2010-132605 | 6/2010 |
| JP | 4689340 | 2/2011 |
| JP | 2011-194675 | 10/2011 |
| JP | 5032133 | 7/2012 |
| WO | WO 2016/012414 A1 | 1/2016 |

OTHER PUBLICATIONS

BP Kumar, IS Chandiran, B Bhavya, M Sindhuri. "Microparticulate Drug Delivery System: A Review." Indian Journal of Pharmaceutical Science & Research, vol. 1 Issue 1, 2011, pp. 19-37. (Year: 2011).*

Y Ke, GS Liu, T Guo, Y Zhang, C Li, W Xue, G Wu, J Wang, C Du. "Size Controlling of Monodisperse Carboxymethyl Cellulose Microparticles via a Microfluidic Process." Journal of Applied Polymer Science, 2014, DOI: 10.1002/app.40663, pp. 1-8. (Year: 2014).*

Srikonda Venkateswara Sastry, Janaki Ram Nyshadham and Joseph A. Fix. "Recent technological advances in oral drug delivery—a review." Pharmaceutical Science & Technology Today, vol. 3, No. 4 Apr. 2000, pp. 138-145. (Year: 2000).*

International Search Report dated May 19, 2017 for counterpart International Patent Application No. PCT/JP2017/008384 filed Mar. 2, 2017.

Written Opinion dated May 19, 2017 for counterpart International Patent Application No. PCT/JP2017/008384 filed Mar. 2, 2017.

* cited by examiner

[Fig. 1]
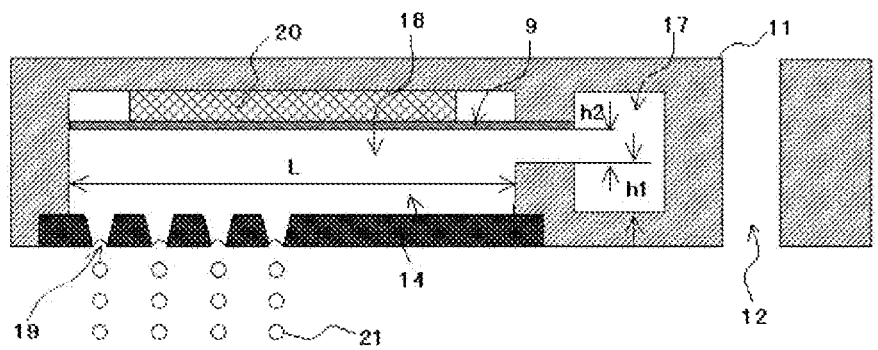
[Fig. 2]
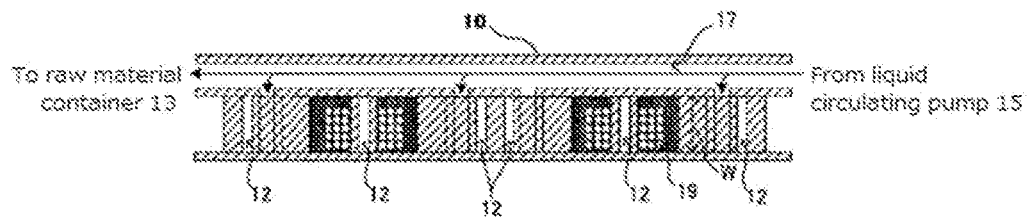
[Fig. 3A]
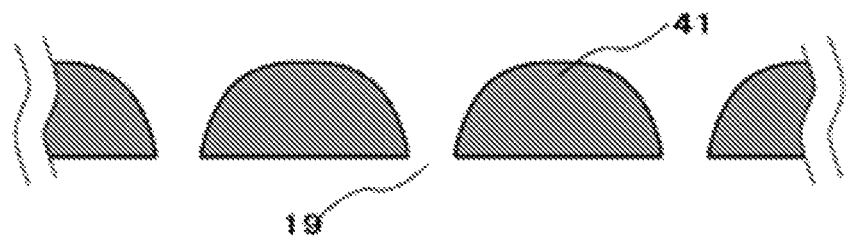
[Fig. 3B]
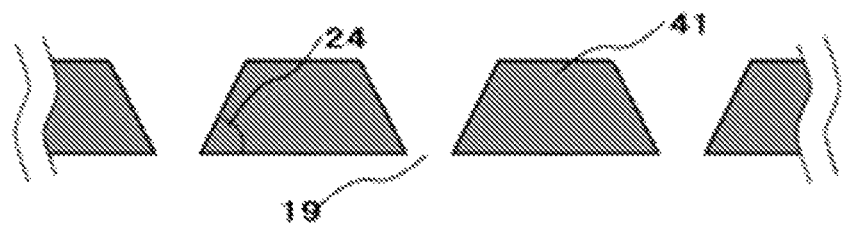
[Fig. 3C]
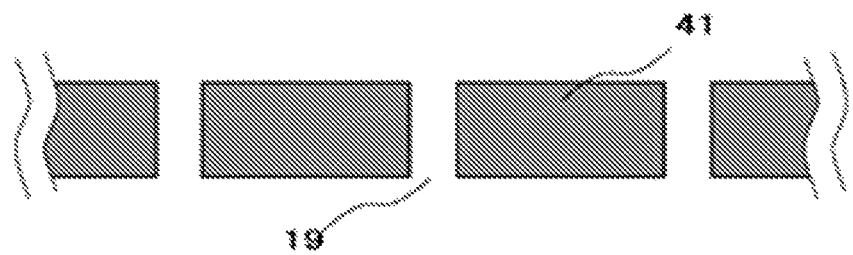

[Fig. 3D]
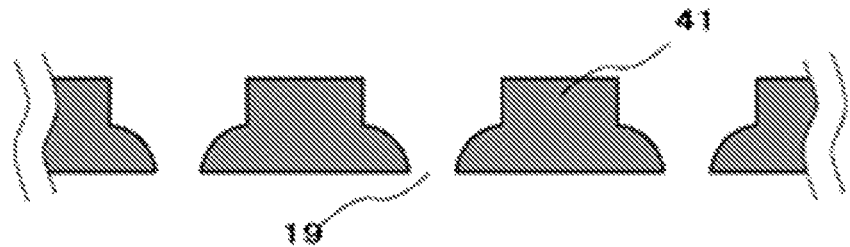
[Fig. 4A]
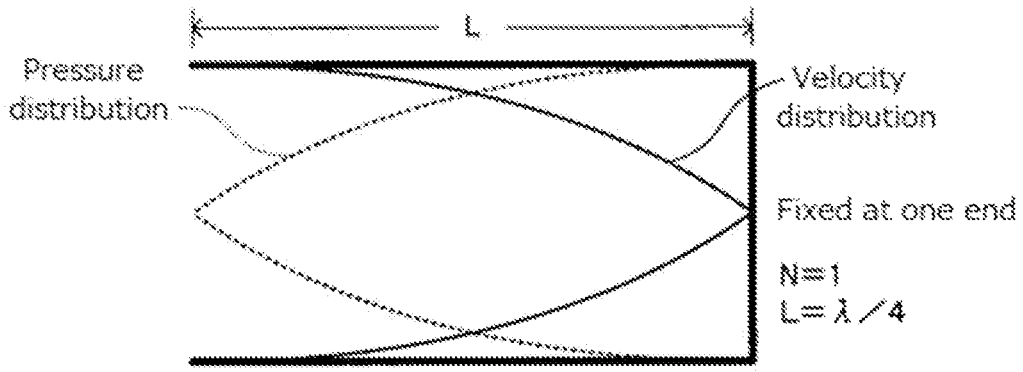
[Fig. 4B]
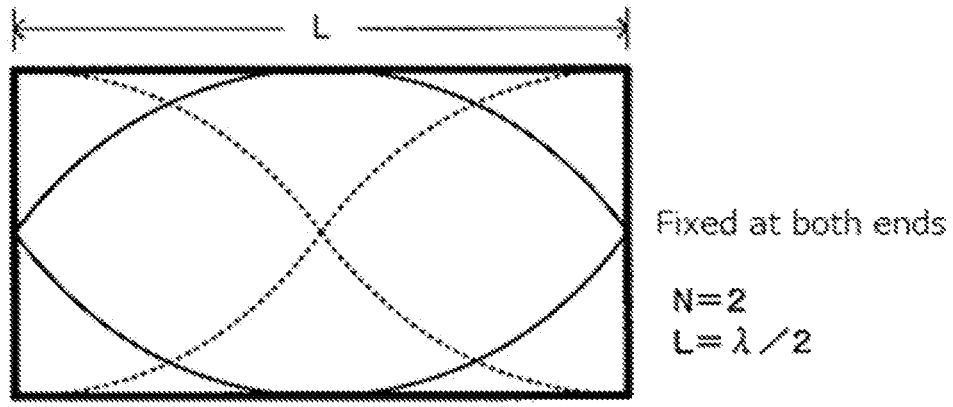
[Fig. 4C]
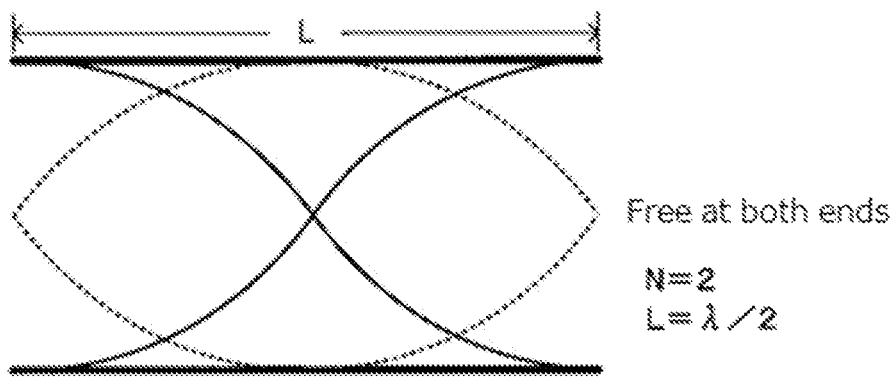

[Fig. 4D]
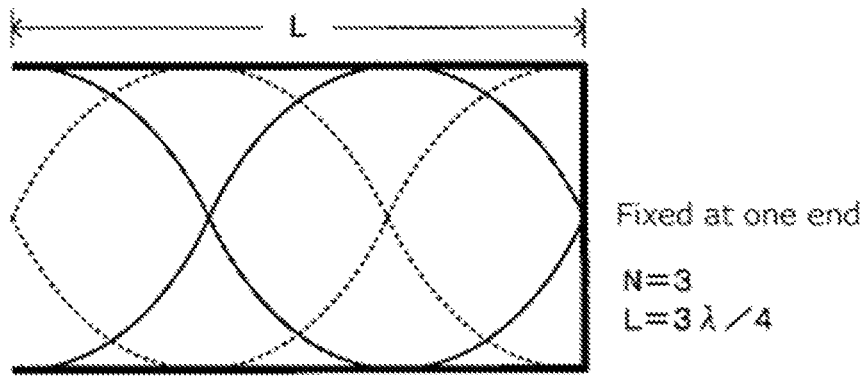
[Fig. 5A]
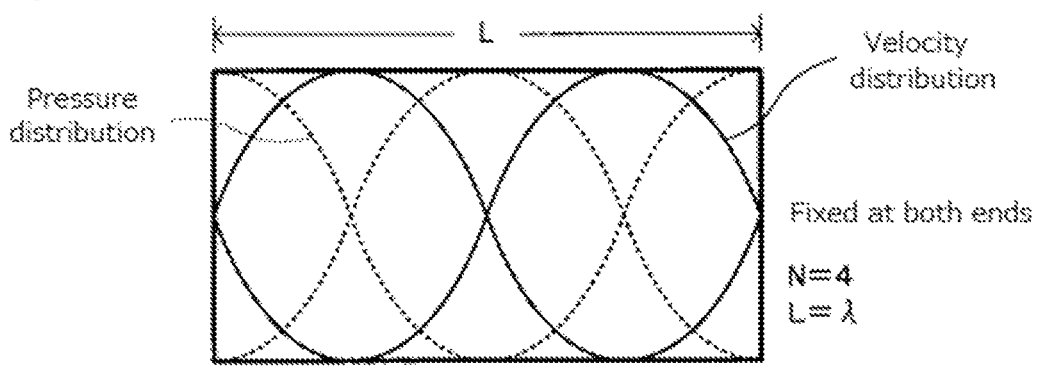
[Fig. 5B]
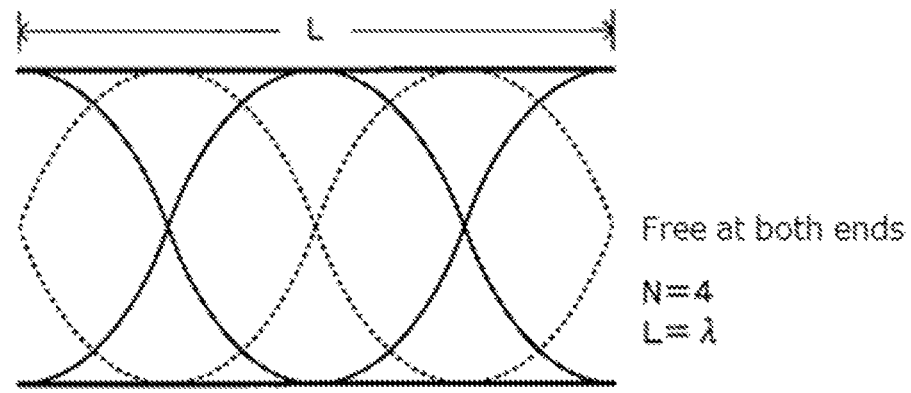
[Fig. 5C]
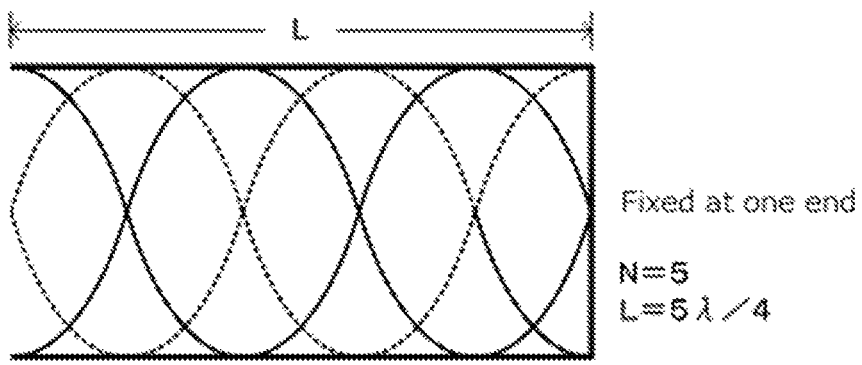

[Fig. 6A]
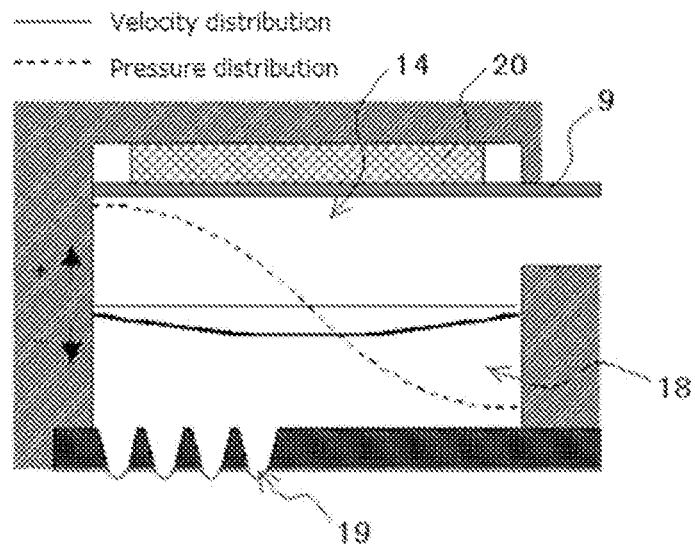
[Fig. 6B]
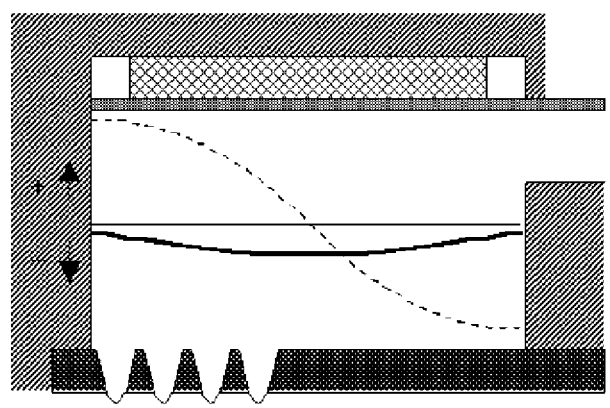
[Fig. 6C]
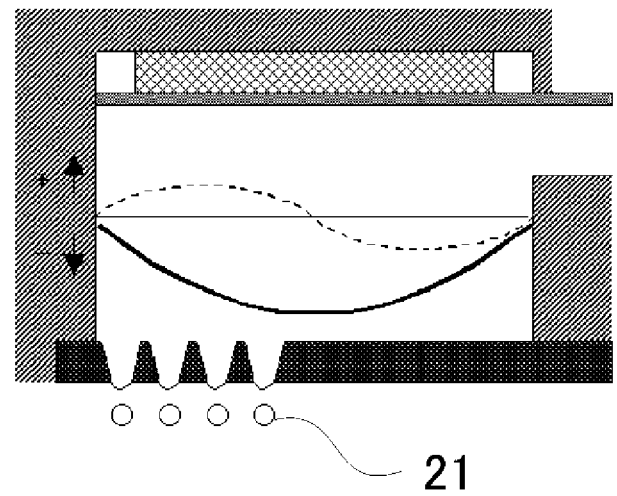

[Fig. 6D]
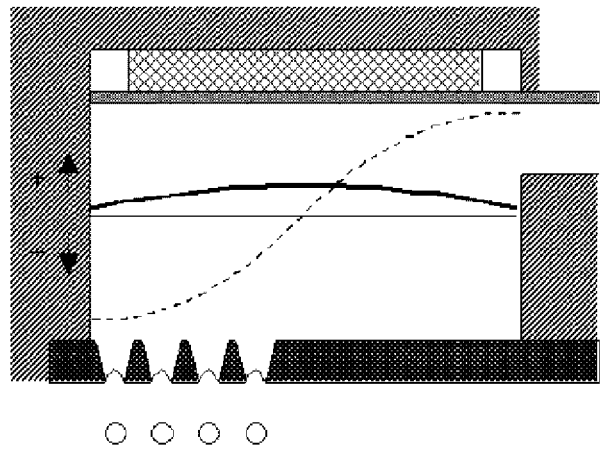
[Fig. 6E]
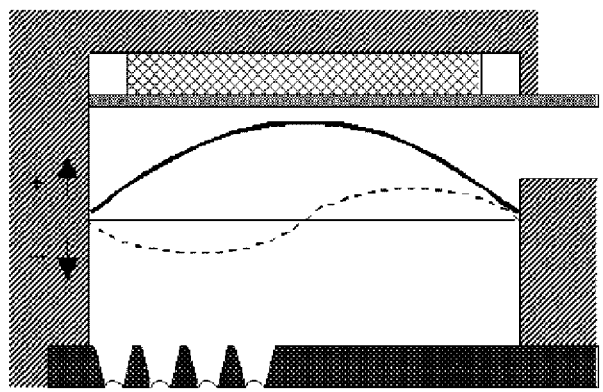

[Fig. 7]
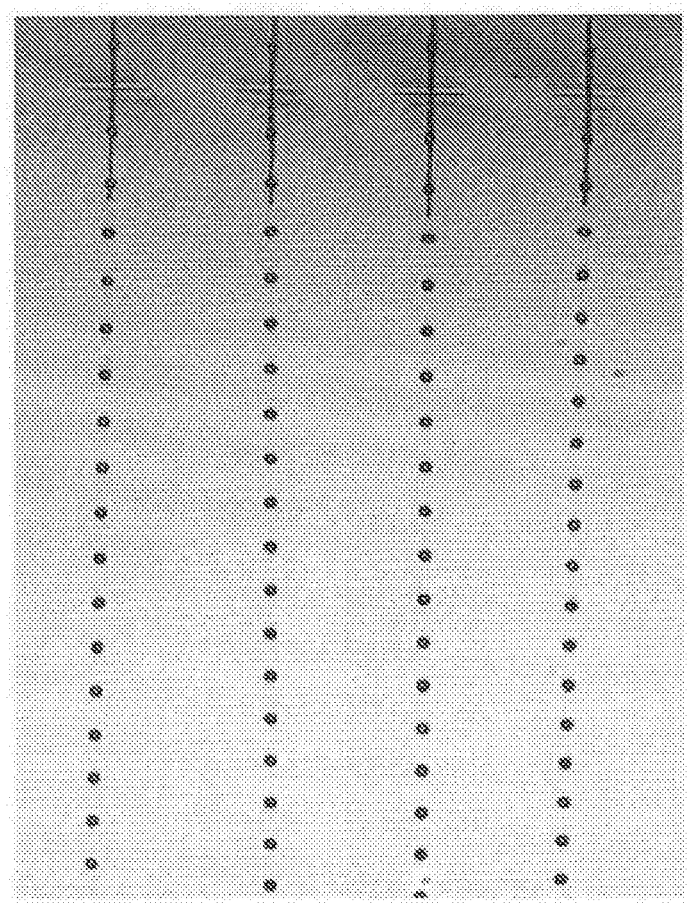
[Fig. 8]
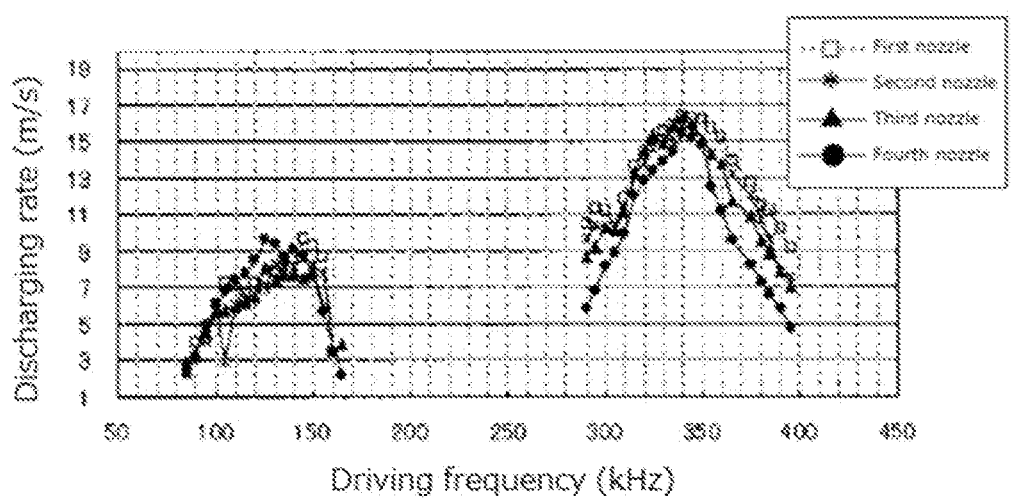

[Fig. 9]
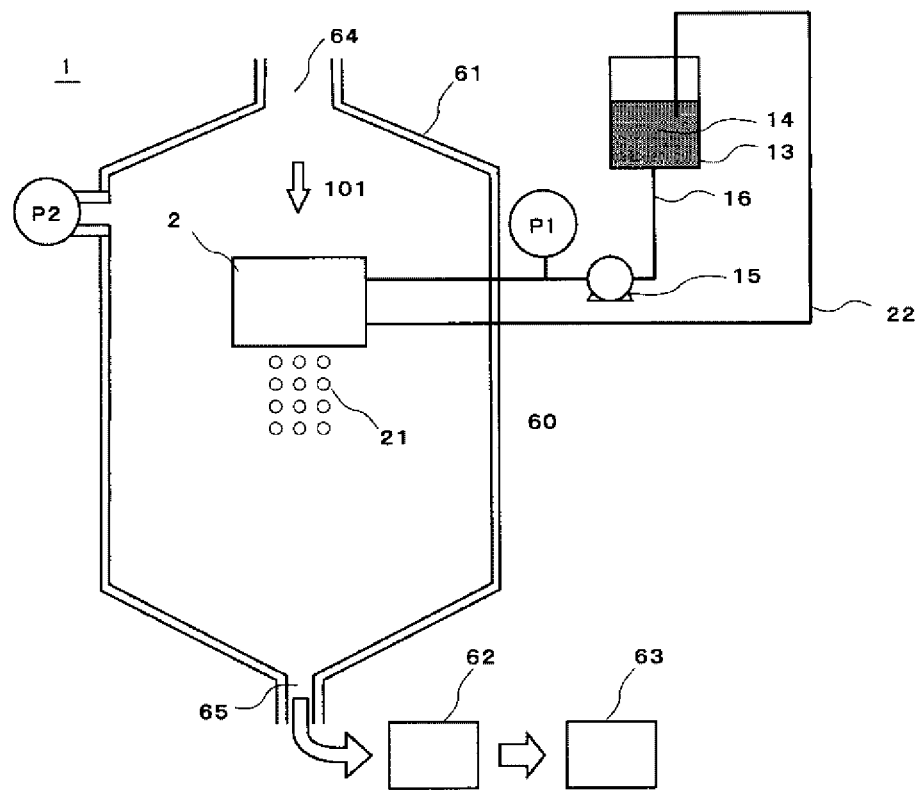
[Fig. 10]
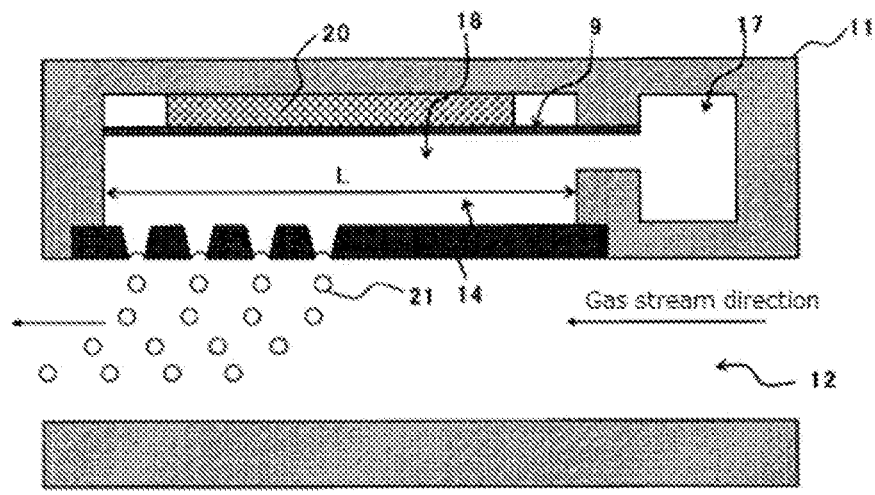

[Fig. 11]
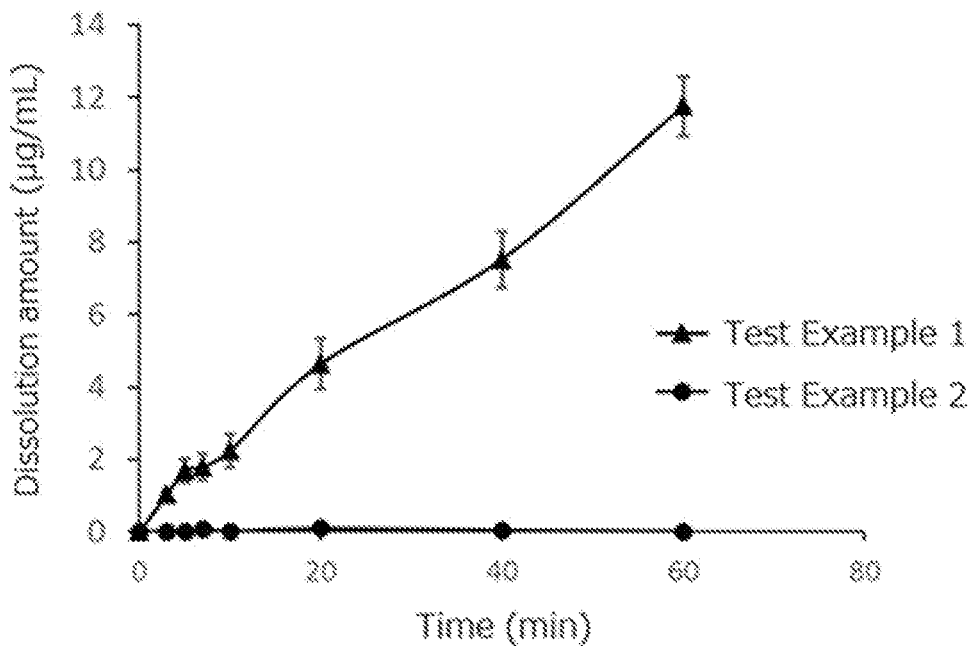
[Fig. 12]
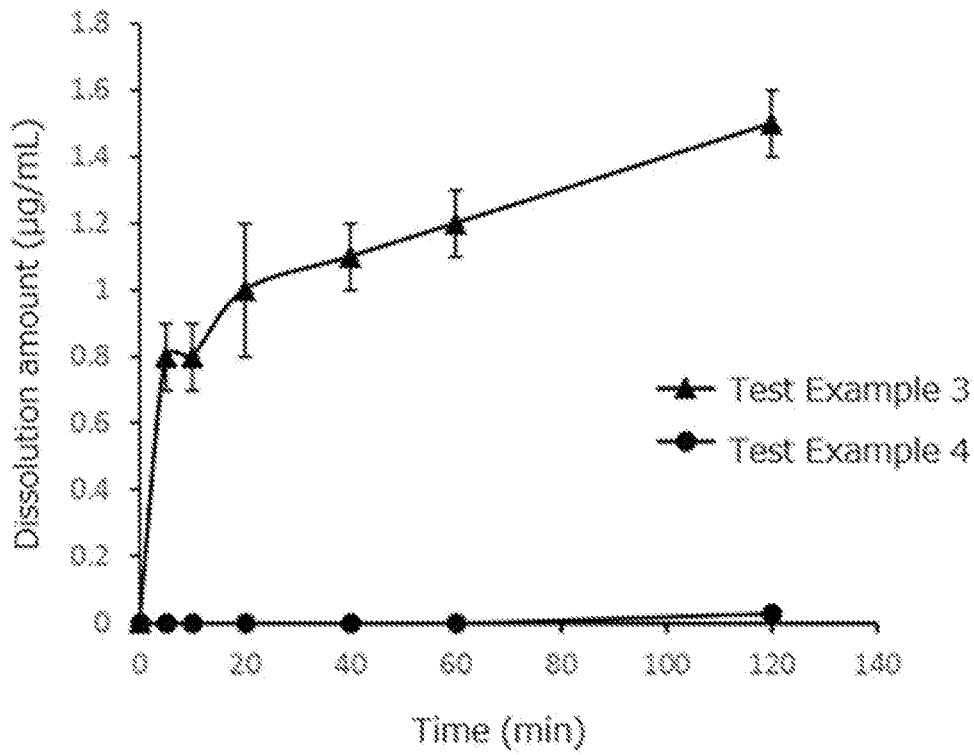

[Fig. 13]
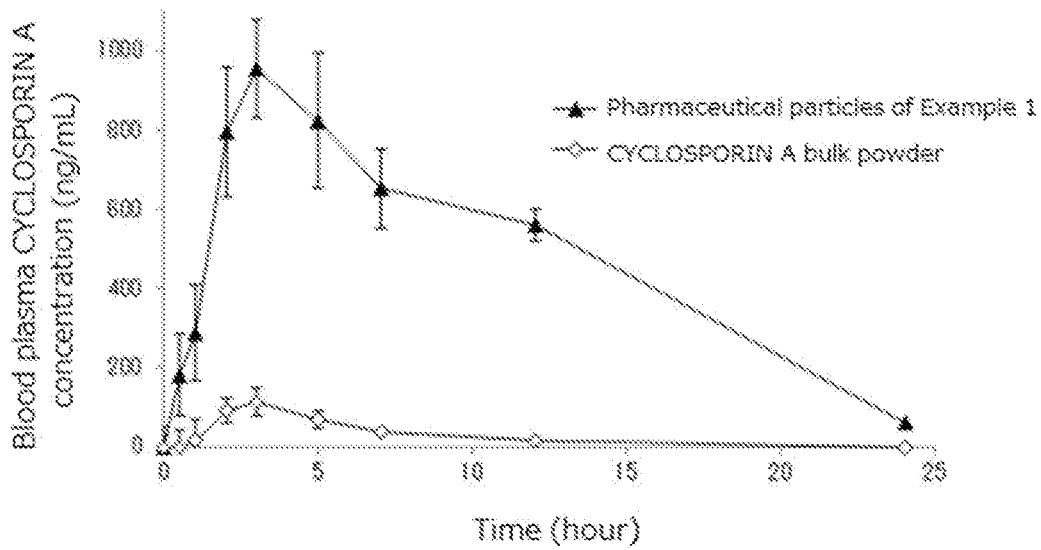
[Fig. 14]
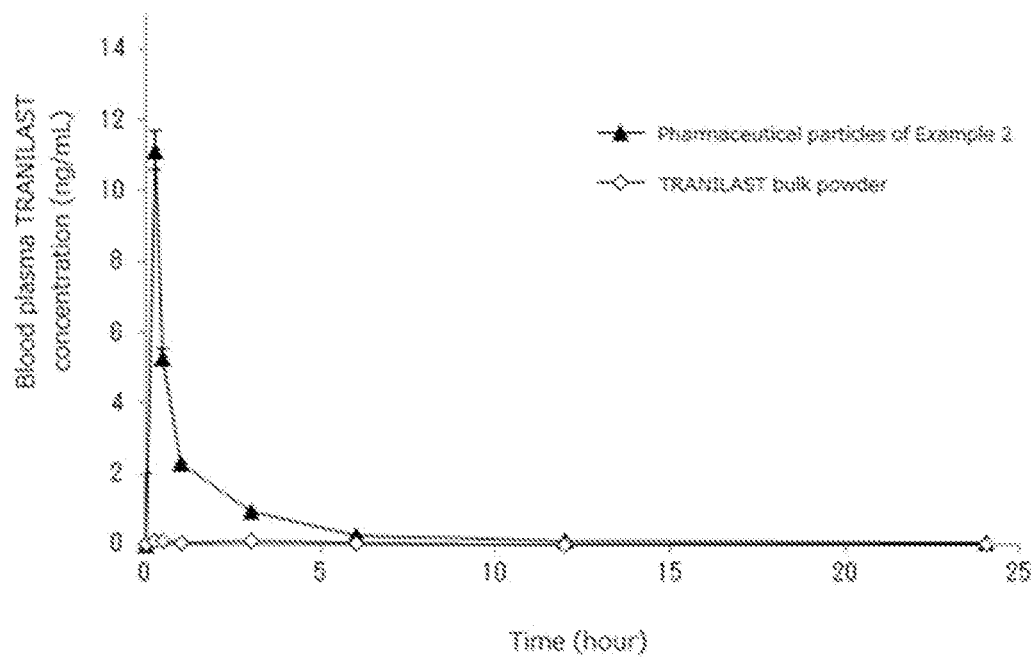

[Fig. 15]
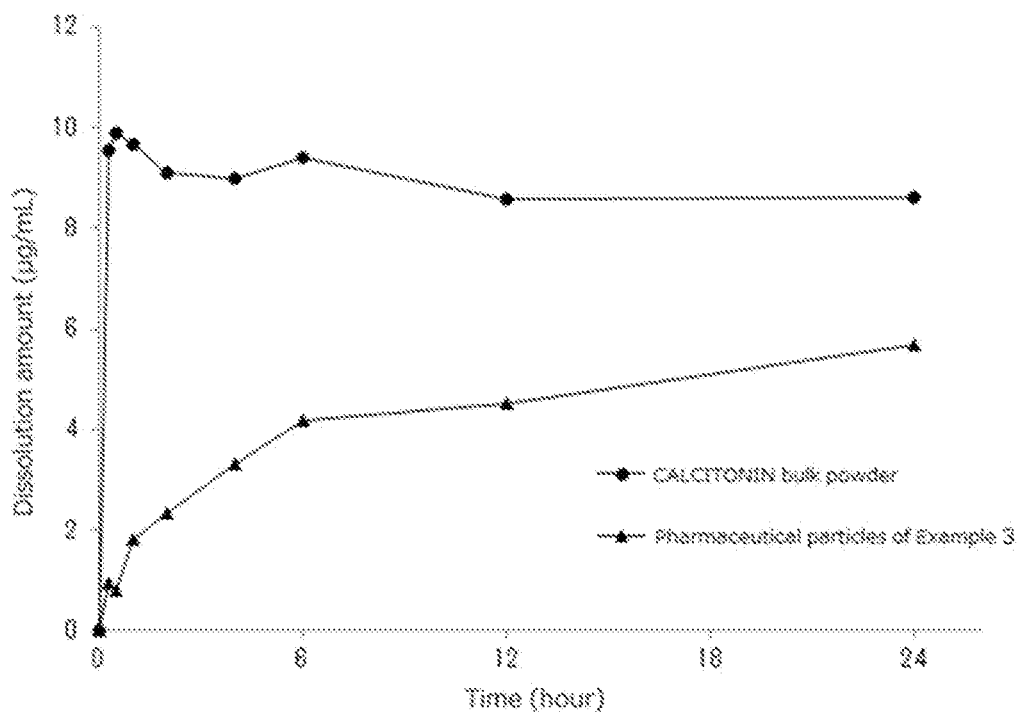
[Fig. 16]
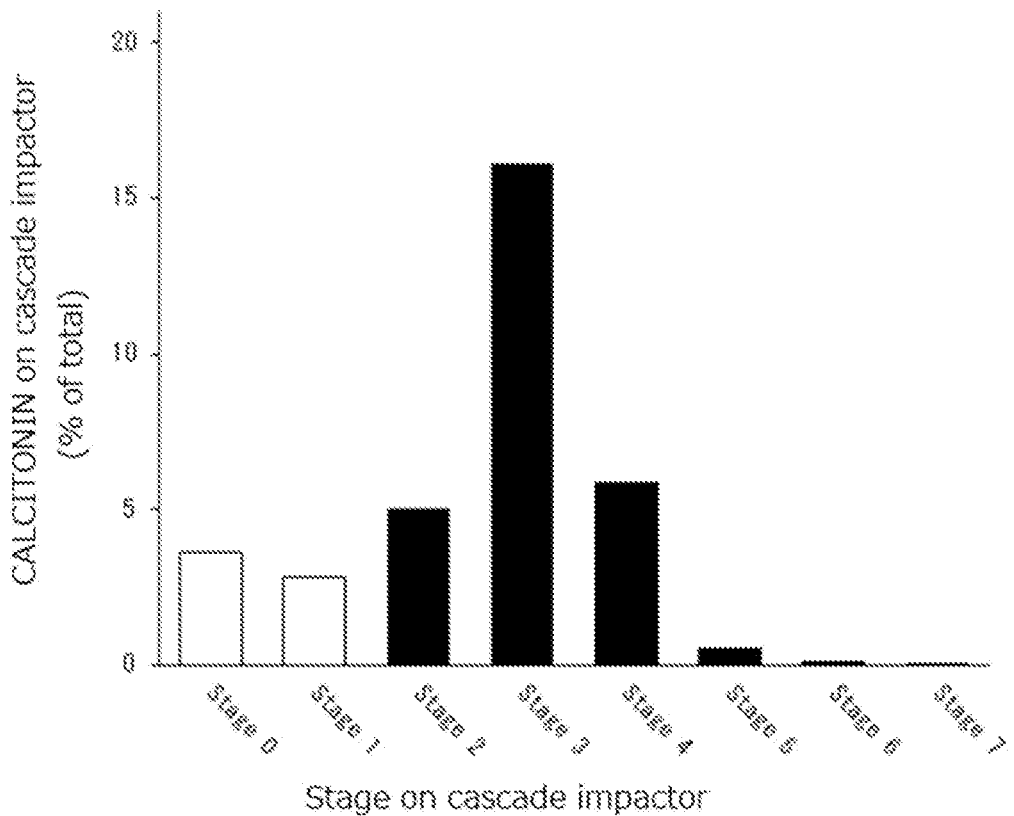

[Fig. 17]
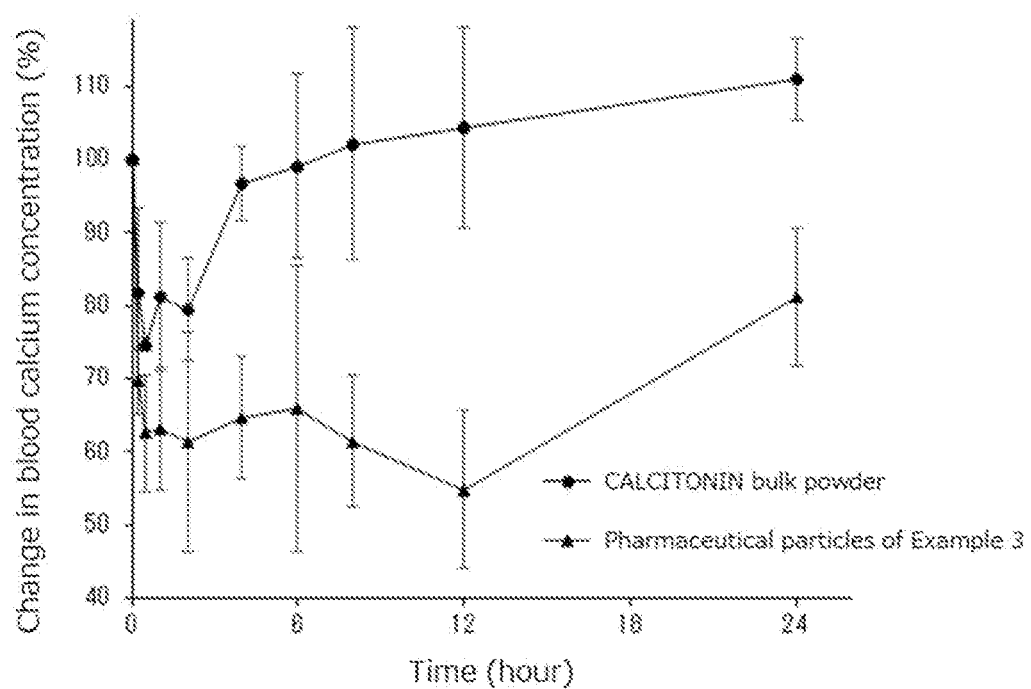

METHOD FOR PRODUCING PARTICLES

TECHNICAL FIELD

The present invention relates to a method for producing particles.

BACKGROUND ART

Particles such as pharmaceutical particles have been produced by dispersing physiologically active substances such as pharmaceutical compounds with dispersing agents.

Examples of methods for producing the particles such as the pharmaceutical particles include pulverization methods and emulsification methods.

In the pulverization methods, the particles are obtained by pulverizing the physiologically active substances such as the pharmaceutical compounds using a variety of mills, optionally with the addition of the dispersing agents or a variety of pulverizing media (e.g., zirconium silicate and glass) typically in the form of spherical beads. In addition, various methods including a variety of pulverization techniques such as airjet pulverization and wet pulverization have been used.

The pulverization methods are advantageous in that the particles such as the pharmaceutical particles are capable of being obtained easily and conveniently. However, the pulverization methods have the problems described below. Firstly, it is difficult to allow the particles such as the pharmaceutical particles to have a smaller particle diameter. Secondly, the resultant particles such as the pharmaceutical particles have a wider particle size distribution. Thirdly, bioavailability is not improved when the pharmaceutical particles are orally administered.

In the emulsification methods, oil phases including the physiologically active substances such as the pharmaceutical compounds, the dispersing agents, and surfactants are added to and dispersed into aqueous phases. Then, the thus-produced dispersion liquid is dried to obtain the particles such as the pharmaceutical particles. The emulsification methods are advantageous in that the particles having a small particle diameter are capable of being produced relatively easily and conveniently. However, the emulsification methods have the problem that only pharmaceutically available surfactants are capable of being used as the surfactants. Moreover, when the oil phases include water-soluble materials, the water-soluble materials migrate from the oil phases to the aqueous phases. As a result, the resultant particles such as pharmaceutical particles are not capable of being controlled in particle diameter, resulting in a wider particle size distribution. Therefore, bioavailability is not improved when the pharmaceutical particles are orally administered.

Therefore, there have been proposed, as methods for solving the aforementioned problems, methods for producing pharmaceuticals in which pharmaceutical particles are produced using spray-drying methods (see, for example, PTLs 1 and 2).

CITATION LIST

Patent Literature

PTL 1: Japanese Unexamined Patent Application Publication No. 2008-100997
PTL 2: Japanese Patent No. 4293572

SUMMARY OF INVENTION

Technical Problem

The present invention has an object to provide a method for producing particles, the method allowing particles which have a narrow particle size distribution to be efficiently obtained and being excellent in continuous productivity.

Solution to Problem

A method for producing particles of the present invention as a means for solving the aforementioned problems includes applying vibration to a liquid including a physiologically active substance and included in a liquid-column resonance liquid-chamber to form a standing wave based on liquid column resonance, to thereby discharge the liquid from at least one discharging port, which is formed in an amplitude direction of the standing wave, to at least one region corresponding to at least one anti-node of the standing wave; and drying the liquid discharged, to thereby form particles.

Advantageous Effects of Invention

The present invention is capable of providing a method for producing particles, the method allowing particles which have a narrow particle size distribution to be efficiently obtained and being excellent in continuous productivity.

BRIEF DESCRIPTION OF DRAWINGS

FIG. 1 is a cross-sectional view illustrating one exemplary liquid-column resonance liquid-droplet discharging section.

FIG. 2 is a cross-sectional view illustrating one exemplary liquid-column resonance liquid-droplet discharging unit.

FIG. 3A is a schematic view illustrating one exemplary structure of discharging holes.

FIG. 3B is a schematic view illustrating another exemplary structure of discharging holes.

FIG. 3C is a schematic view illustrating another exemplary structure of discharging holes.

FIG. 3D is a schematic view illustrating another exemplary structure of discharging holes.

FIG. 4A is a schematic view illustrating a standing wave of velocity fluctuation and a standing wave of pressure fluctuation when N=1 and one end is fixed.

FIG. 4B is a schematic view illustrating a standing wave of velocity fluctuation and a standing wave of pressure fluctuation when N=2 and both ends are fixed.

FIG. 4C is a schematic view illustrating a standing wave of velocity fluctuation and a standing wave of pressure fluctuation when N=2 and both ends are free.

FIG. 4D is a schematic view illustrating a standing wave of velocity fluctuation and a standing wave of pressure fluctuation when N=3 and one end is fixed.

FIG. 5A is a schematic view illustrating a standing wave of velocity fluctuation and a standing wave of pressure fluctuation when N=4 and both ends are fixed.

FIG. 5B is a schematic view illustrating a standing wave of velocity fluctuation and a standing wave of pressure fluctuation when N=4 and both ends are free.

FIG. 5C is a schematic view illustrating a standing wave of velocity fluctuation and a standing wave of pressure fluctuation when N=5 and one end is fixed.

FIG. 6A is a schematic view illustrating one exemplary pressure and velocity waveforms in a liquid-column resonance liquid-chamber when liquid droplets are discharged.

FIG. 6B is a schematic view illustrating another exemplary pressure and velocity waveforms in a liquid-column resonance liquid-chamber when liquid droplets are discharged.

FIG. 6C is a schematic view illustrating another exemplary pressure and velocity waveforms in a liquid-column resonance liquid-chamber when liquid droplets are discharged.

FIG. 6D is a schematic view illustrating another exemplary pressure and velocity waveforms in a liquid-column resonance liquid-chamber when liquid droplets are discharged.

FIG. 6E is a schematic view illustrating another exemplary pressure and velocity waveforms in a liquid-column resonance liquid-chamber when liquid droplets are discharged.

FIG. 7 is an image illustrating exemplary actual liquid droplets discharged by a liquid-column resonance liquid-droplet discharging section.

FIG. 8 is a graph illustrating dependency of a liquid-droplet discharging velocity on a driving frequency.

FIG. 9 is a schematic view illustrating one exemplary particle producing apparatus.

FIG. 10 is a schematic view illustrating one exemplary gas stream path.

FIG. 11 is a graph illustrating the evaluation results for a dissolution property in Test Examples 1 and 2.

FIG. 12 is a graph illustrating the evaluation results for a dissolution property in Test Examples 3 and 4.

FIG. 13 is a graph illustrating the evaluation results for an oral absorbability in Test Examples 5 and Example 1.

FIG. 14 is a graph illustrating the evaluation results for an oral absorbability in Test Examples 6 and Example 2.

FIG. 15 is a graph illustrating the evaluation results for a dissolution property in Test Examples 7 and Example 3.

FIG. 16 is a graph illustrating the evaluation results for an inhalation property in Example 3.

FIG. 17 is a graph illustrating the evaluation results for a drug efficacy in Test Examples 9 and Example 3.

DESCRIPTION OF EMBODIMENTS (Method for Producing Particles)

A method for producing particles of the present invention includes a discharging step and a particle forming step; and, if necessary, further includes other steps.

There is a need to produce particles having a smaller particle diameter and a narrow particle size distribution in particle diameter in order to improve properties such as a handling ability, a dissolution rate, and variation in dissolution amount of the resultant particles. However, methods for producing particles using the spray-drying method known in the art have the same problem as the pulverization methods. That is, particles having a narrow particle size distribution in particle diameter are not capable of being produced. The method for producing particles of the present invention is based on the above-described finding. The method for producing particles of the present invention is capable of being used to efficiently produce particles having a smaller particle diameter and a narrow particle size distribution in particle diameter.

Note that, the "particles" may be referred to as "powder."

<Discharging Step>

The discharging step is a step of applying vibration to a liquid including a physiologically active substance and included in a liquid-column resonance liquid-chamber to form a standing wave based on liquid column resonance, to thereby discharge the liquid from at least one discharging port, which is formed in an amplitude direction of the standing wave, to at least one region corresponding to at least one anti-node of the standing wave. That is, in the discharging step, a liquid-column resonance method is capable of being suitably used.

<Liquid>

The liquid includes a physiologically active substance; and, if necessary, further includes a dispersing agent, a solvent, and optionally other components.

-Physiologically Active Substance-

The physiologically active substance is not particularly limited and may be appropriately selected depending on the intended purpose. Examples of the physiologically active substance include pharmaceutical compounds, functional food compounds, and functional cosmetic compounds.

Particles produced by the liquid-column resonance method using a liquid including the pharmaceutical compounds, the functional food compounds, or the functional cosmetic compounds are capable of being suitably used for, for example, pharmaceuticals, food, or cosmetics.

--Pharmaceuticals--

The pharmaceuticals include a pharmaceutical compound; and, if necessary, further include a dispersing agent, an additive, and other components.

The pharmaceuticals are not particularly limited and may be appropriately selected depending on the intended purpose. Examples of the pharmaceuticals include tablets, capsules, suppositories, and other solid dosage forms; aerosol for intranasal or pulmonary administration; and solutions for injection, intraocular administration, intraaural administration, or oral administration.

The particles are capable of being mixed with, for example, the dispersing agent and the additive to be formed into functional particles or a pharmaceutical composition.

The functional particles are not particularly limited and may be appropriately selected depending on the intended purpose. Examples of the functional particles include immediate release particles, sustained release particles, pH-dependent release particles, pH-independent release particles, enteric coated particles, particles with a release control coating, and particles including nanocrystal. These may be used alone or in combination.

The pharmaceutical compositions are not particularly limited and may be appropriately selected depending on the intended purpose. Examples of the pharmaceutical compositions include colon delivery preparations, lipid microsphere preparations, dry emulsion preparations, self-emulsifying preparations, dry syrup, powder preparations for transnasal administration, powder preparations for transpulmonary administration, wax matrix preparations, hydrogel preparations, polymeric micelle preparations, mucoadhesive preparations, gastric floating preparations, liposome preparations, and solid dispersion preparations. These may be used alone or in combination.

Note that, the pharmaceuticals may be pharmaceutical compositions or bulk drugs.

---Pharmaceutical Compound---

The pharmaceutical compounds used for the pharmaceuticals are not particularly limited and may be appropriately selected depending on the intended purpose, as long as the pharmaceutical compounds are capable of being formed into the functional particles or the pharmaceutical compositions.

Specifically, for example, poorly water-soluble compounds to be added to solid dispersions are capable of being formed into particles using the method for producing particles of the present invention to improve bioavailability even when orally administered. The poorly water-soluble compounds refer to compounds having a water/octanol distribution coefficient (Log P) of 3 or more. Meanwhile, water-soluble compounds refer to compounds having a water/octanol distribution coefficient (Log P) of less than 3. The water/octanol distribution coefficient may be measured according to JIS Z 7260-107 (2000) Shake flask method. The pharmaceutical compounds may be in any form such as salts and hydrates, as long as the pharmaceutical compounds are effective as pharmaceuticals.

The water-soluble compounds are not particularly limited and may be appropriately selected depending on the intended purpose. Examples of the water-soluble compounds include abacavir, acetaminophen, acyclovir, amiloride, amitriptyline, antipyrine, atropine, buspirone, caffeine, captopril, chloroquine, chlorpheniramine, cyclophosphamide, desipramine, diazepam, diltiazem, diphenhydramine, disopyramide, doxine, doxycycline, enalapril, ephedrine, ethambutol, ethinylestradiol, fluoxetine, imipramine, glucose, ketorol, ketoprofen, labetalol, levodopa, levofloxacin, metoprolol, metronidazole, midazolam, minocycline, misoprostol, metformin, nifedipine, phenobarbital, prednisolone, promazine, propranolol, quinidine, rosiglitazone, salicylic acid, theophylline, valproic acid, verapamil, zidovudine, and calcitonin. These may be used alone or in combination.

The poorly water-soluble compounds are not particularly limited and may be appropriately selected depending on the intended purpose. Examples of the poorly water-soluble compounds include griseofulvin, itraconazole, norfloxacin, tamoxifen, cyclosporine, glibenclamide, troglitazone, nifedipine, phenacetin, phenytoin, digitoxin, nilvadipine, diazepam, chloramphenicol, indomethacin, nimodipine, dihydroergotoxine, cortisone, dexamethasone, naproxen, tulobuterol, beclometasone dipropionate, fluticasone propionate, pranlukast, tranilast, loratadine, tacrolimus, amprenavir, bexarotene, calcitriol, clofazimine, digoxin, doxercalciferol, dronabinol, etopodide, isotretinoin, lopinavir, ritonavir, progesterone, saquinavir, sirolimus, tretinoin, valproic acid, amphotericin, fenoldopam, melphalan, paricalcitol, propofol, voriconazole, ziprasidone, docetaxel, haloperidol, lorazepam, teniposide, testosterone, valrubicin, quercetin, and allopurinol. Among them, cyclosporine and tranilast are preferable, and cyclosporine is more preferable.

An amount of the pharmaceutical compounds is preferably 5% by mass or more but 95% by mass or less, more preferably 5% by mass or more but 50% by mass or less relative to the total amount of the particles of the present invention. The amount of 5% by mass or more but 95% by mass or less is advantageous in that the pharmaceutical compound is administered at a dosage appropriate as a pharmaceutical composition and a pharmaceutical component is easily redispersed in water by the action of the dispersing agent.

--Functional Food Compound--

The functional food compounds are not particularly limited and may be appropriately selected depending on the intended purpose. Examples of the functional food compounds include vitamin A, vitamin D, vitamin E, lutein, zeaxanthin, lipoic acids, flavonoids, and fatty acids (e.g., omega-3 fatty acids and omega-6 fatty acids). These may be used alone or in combination.

--Food--

The food includes the functional food compounds; and, if necessary, further includes a dispersing agent, an additive, and other components.

The food is not particularly limited and may be appropriately selected depending on the intended purpose. Examples of the food include frozen desserts such as ice cream, ice sherbet, and shaved ice; noodles such as buckwheat noodles, Udon noodles, beanstarch vermicelli, thick dumpling skin, thin dumpling skin, Chinese noodles, and instant noodles; confectionery such as candy, chewing gum, chocolate, tablet confectionery, snack food, biscuits, jelly, jam, cream, baked confectionery, and bread; sea food such as crab, salmon, clam, tuna, sardine, shrimp, bonito, mackerel, whale, oyster, saury, squid, ark shell, scallop, abalone, sea urchin, salmon roe, and small abalone; processed sea food or processed meat food such as surimi, ham, and sausage; dairy products such as processed milk and yogurt; oils and fats and processed oils and fats such as salad oils, tempura oils, margarine, mayonnaise, shortening, whipped cream, and dressing; condiments such as sauce; retort pouch food such as curry roux, stew, Oyakodon (rice bowl topped with chicken and eggs), Kayu (rice gruel), Zozui (rice porridge with meat, seafood, or vegetables), Chukadon (rice bowl topped with chop suey), Katsudon (rice bowl topped with pork cutlet), Tendon (rice bowl topped with tempera), Unadon (rice bowl topped with grilled eel), Hayashi-rice (hashed beef with rice), Oden (Japanese hotchpotch), Mapo tofu, Gyudon (rice bowl topped with beef), meat sauce, egg soup, Omurice (omelet with a filling of ketchup-seasoned fried rice), dim sum, hamburg steak, and meatball; and health food and dietary supplement in various forms.

--Functional Cosmetic Compound--

The functional cosmetic compounds are not particularly limited and may be appropriately selected depending on the intended purpose. Examples of the functional cosmetic compounds include alcohols, fatty alcohols, and polyols, aldehydes, alkanol amines, alkoxylated alcohols (e.g., polyethylene glycol derivatives of alcohols or fatty alcohols), alkoxylated amides, alkoxylated amines, alkoxylated carboxylic acids, amides including salts of the amides (e.g., ceramides), amines, amino acids including salts and alkyl-substituted derivatives of the amino acids, esters, alkyl-substituted and acyl derivatives, polyacrylic acids, acrylamide copolymers, adipic acid copolymer aqueous solution, amino silicones, biological polymers and derivatives of the biological polymers, butylene copolymers, hydrocarbons (e.g., polysaccharides, chitosans, derivatives of the polysaccharides or chitosans), carboxylic acids, carbomers, esters, ethers, and polymeric ethers (e.g., PEG derivatives and PPG derivatives), glyceryl esters and derivatives of the glyceryl esters, halogen compounds, heterocyclic compounds including salts of the heterocyclic compounds, hydrophilic colloids and derivatives including salt and gum of the hydrophilic colloids (e.g., cellulose derivatives, gelatin, xanthan gum, natural rubber), imidazolines, inorganic materials (clay, $TiO_2$, ZnO), ketones (e.g., camphor), isethionates, lanolin and derivatives of the lanolin, organic salts, phenols including salts of the phenols (e.g., parabens), phosphorus compounds (e.g., phosphoric acid derivatives), polyacrylates and acrylate polymers, protein and enzyme derivatives (e.g., collagen), synthetic polymers including salts of the synthetic polymers, siloxanes and silanes, sorbitan derivatives, sterols, sulfonic acids and derivatives of the sulfonic acids, and waxes. These may be used alone or in combination.

--Cosmetics--

The cosmetics include a functional cosmetic compound; and, if necessary, a dispersing agent, an additive, and other components.

The cosmetics are not particularly limited and may be appropriately selected depending on the intended purpose. Examples of the cosmetics include skin care cosmetics, make-up cosmetics, hair care cosmetics, body care cosmetics, and fragrance cosmetics.

The skin care cosmetics are not particularly limited and may be appropriately selected depending on the intended purpose. Examples of the skin care cosmetics include cleansing compositions for removing make-up, face washes, milky lotions, skin lotions, serums, skin moisturizers, facial masks, and shaving cosmetics (e.g., shaving foams, pre-shave lotions, and after-shave lotions).

The make-up cosmetics are not particularly limited and may be appropriately selected depending on the intended purpose. Examples of the make-up cosmetics include foundation, lip sticks, and mascaras.

The hair care cosmetics are not particularly limited and may be appropriately selected depending on the intended purpose. Examples of the hair care cosmetics include hair shampoos, hair rinses, hair conditioners, hair treatments, and hair dressings (e.g., hair gels, hair set lotions, hair styling liquids, and hair mists).

The body care cosmetics are not particularly limited and may be appropriately selected depending on the intended purpose. Examples of the body care cosmetics include body soaps, sunscreen cosmetics, and massage creams.

The fragrance cosmetics are not particularly limited and may be appropriately selected depending on the intended purpose. Examples of the fragrance cosmetics include scent (e.g., perfume and parfum), eau de parfum (e.g., perfume cologne), eau de toilette (e.g., perfume de toilette and parfum de toilette), eau de cologne (e.g., cologne and fresh cologne).

-Dispersing Agent-

The dispersing agent is capable of being suitably used for dispersing the physiologically active substance.

The dispersing agent may be a low-molecular-weight dispersing agent or a high-molecular-weight polymeric dispersing agent.

The low-molecular-weight dispersing agent refers to compounds having a weight average molecular weight of less than 15,000. The high-molecular-weight polymeric dispersing agent refers to compounds including covalent bonds between one or more monomers repeatedly and having a weight average molecular weight of 15,000 or more.

The low-molecular-weight dispersing agent is not particularly limited and may be appropriately selected depending on the intended purpose, as long as the low-molecular-weight dispersing agent is acceptable as the physiologically active substance for, for example, pharmaceuticals. Examples of the low-molecular-weight dispersing agent include lipids, saccharides, cyclodextrins, amino acids, and organic acids. These may be used alone or in combination.

The lipids are not particularly limited and may be appropriately selected depending on the intended purpose. Examples of the lipids include mid-chain or long-chain monoglycerides, mid-chain or long-chain diglycerides, or mid-chain or long-chain triglycerides, phospholipids, vegetable oils (e.g., soybean oils, avocado oils, squalene oils, sesame oils, olive oils, corn oils, rapeseed oils, safflower oils, and sunflower oils), fish oils, seasoning oils, water-insoluble vitamins, fatty acids, and mixtures of the above-described lipids. These may be used alone or in combination.

The saccharides are not particularly limited and may be appropriately selected depending on the intended purpose. Examples of the saccharides include glucose, mannose, idose, galactose, fucose, ribose, xylose, lactose, sucrose, maltose, trehalose, turanose, raffinose, maltotriose, acarbose, or sugar alcohols, glycerin, sorbitol, lactitol, maltitol, mannitol, xylitol, erythritol or polyols, or derivatives of the above-described saccharides. These may be used alone or in combination.

The cyclodextrins are not particularly limited and may be appropriately selected depending on the intended purpose. Examples of the cyclodextrins include hydroxypropyl-beta-cyclodextrin, beta-cyclodextrin, gamma-cyclodextrin, alpha-cyclodextrin, or cyclodextrin derivatives. These may be used alone or in combination.

The amino acids are not particularly limited and may be appropriately selected depending on the intended purpose. Examples of the amino acids include valine, lysine, leucine, threonine, isoleucine, asparagine, glutamine, phenylalanine, aspartic acid, serine, glutamic acid, methionine, arginine, glycine, alanine, tyrosine, proline, histidine, cysteine, tryptophan, or derivatives of the above-described amino acids. These may be used alone or in combination.

The organic acids are not particularly limited and may be appropriately selected depending on the intended purpose. Examples of the organic acids include adipic acid, ascorbic acid, citric acid, fumaric acid, gallic acid, glutaric acid, lactic acid, malic acid, maleic acid, succinic acid, tartaric acid, or derivatives of the above-described organic acids. These may be used alone or in combination.

The polymeric dispersing agents are not particularly limited and may be appropriately selected depending on the intended purpose. Examples of the polymeric dispersing agents include water-soluble celluloses, polyalkylene glycol, poly(meth)acrylamide, poly(meth)acrylic acid, poly(meth)acrylic ester, polyallylamine, polyvinylpyrrolidone, polyvinyl alcohol, polyvinyl acetate, biodegradable polyesters, polyglycolic acid, polyamino acids, gelatin, polymeric acids, polydioxane, or derivatives of the above-described polymeric dispersing agents. These may be used alone or in combination.

The water-soluble celluloses are not particularly limited and may be appropriately selected depending on the intended purpose. Examples of the water-soluble celluloses include alkyl celluloses such as methyl cellulose and ethyl cellulose; hydroxyalkyl celluloses such as hydroxyethyl cellulose and hydroxypropyl cellulose; and hydroxyalkyl alkyl celluloses such as hydroxyethyl methyl cellulose and hydroxypropyl methyl cellulose. These may be used alone or in combination. Among them, hydroxypropyl cellulose and hydroxypropyl methyl cellulose are preferable and hydroxypropyl cellulose is more preferable from the viewpoint of improvement of solubility.

Products of the hydroxypropyl celluloses having various viscosities are commercially available from various suppliers. The viscosities are believed to depend on a weight average molecular weight, a substitution degree and a molecular weight, or a substitution degree. Any of the products are capable of being used in the present invention.

The weight average molecular weight of the hydroxypropyl cellulose is not particularly limited and may be appropriately selected depending on the intended purpose, but is preferably 15,000 or more but 400,000 or less. Note that, the weight average molecular weight may be measured using gel permeation chromatography (GPC).

A viscosity of a 2% by mass aqueous solution of the hydroxypropyl cellulose (at 20 degrees Celsius) is not particularly limited and may be appropriately selected depending on the intended purpose, but is preferably 2.0 mPa·s (centipoise, cps) or more but 4,000 mPa·s (centipoise, cps) or less.

The hydroxypropyl cellulose may be commercially available products. The commercially available products are not particularly limited and may be appropriately selected depending on the intended purpose. Examples of the commercially available products include HPC-SSL having a molecular weight of 15,000 or more but 30,000 or less and a viscosity of 2.0 mPa·s or more but 2.9 mPa·s or less; HPC-SL having a molecular weight of 30,000 or more but 50,000 or less and a viscosity of 3.0 mPa·s or more but 5.9 mPa·s or less; HPC-L having a molecular weight of 55,000 or more but 70,000 or less and a viscosity of 6.0 mPa·s or more but 10.0 mPa·s or less; HPC-M having a molecular weight of 110,000 or more but 150,000 or less and a viscosity of 150 mPa·s or more but 400 mPa·s or less; and HPC-H having a molecular weight of 250,000 or more but 400,000 or less and a viscosity of 1,000 mPa·s or more but 4,000 mPa·s or less (all available from Nippon Soda Co., Ltd.). These may be used alone or in combination. Among them, HPC-SSL having a molecular weight of 15,000 or more but 30,000 or less and a viscosity of 2.0 mPa·s or more but 2.9 mPa·s or less is preferable.

The polyalkylene glycol is not particularly limited and may be appropriately selected depending on the intended purpose. Examples of the polyalkylene glycol include polyethylene glycol (PEG), polypropylene glycol, polybutylene glycol, or copolymers of the above-described polyalkylene glycol. These may be used alone or in combination.

The poly(meth)acrylamide is not particularly limited and may be appropriately selected depending on the intended purpose. Examples of the poly(meth)acrylamide include N-methyl(meth)acrylamide, N-ethyl(meth)acrylamide, N-propyl(meth)acrylamide, N-butyl(meth)acrylamide, N-benzyl(meth)acrylamide, N-hydroxyethyl(meth)acrylamide, N-phenyl(meth)acrylamide, N-tolyl(meth)acrylamide, N-(hydroxyphenyl)(meth)acrylamide, N-(sulfamoylphenyl)(meth)acrylamide, N-(phenylsulfonyl)(meth)acrylamide, N-(tolylsulfonyl)(meth)acrylamide, N,N-dimethyl(meth)acrylamide, N-methyl-N-phenyl(meth)acrylamide, and N-hydroxyethyl-N-methyl(meth)acrylamide. These may be used alone or in combination.

The poly(meth)acrylic acid is not particularly limited and may be appropriately selected depending on the intended purpose. Examples of the poly(meth)acrylic acid include homopolymers of, for example, polyacrylic acid or polymethacrylic acid; and copolymers such as an acrylic acid-methacrylic acid copolymer. These may be used alone or in combination.

The poly(meth)acrylic ester is not particularly limited and may be appropriately selected depending on the intended purpose. Examples of the poly(meth)acrylic ester include ethylene glycol di(meth)acrylate, di ethylene glycol di(meth)acrylate, propylene glycol di(meth)acrylate, glycerol poly(meth)acrylate, polyethylene glycol(meth)acrylate, trimethylolpropane tri(meth)acrylate, pentaerythritol tetra(meth)acrylate, and 1,3-butylene glycol di(meth)acrylate.

The polyallylamine is not particularly limited and may be appropriately selected depending on the intended purpose. Examples of the polyallylamine include diallylamine and triallylamine. These may be used alone or in combination.

The polyvinylpyrrolidone may be commercially available products. The commercially available products are not particularly limited and may be appropriately selected depending on the intended purpose. Examples of the commercially available products include PLASDONE C-15 (available from ISP TECHNOLOGIES); KOLLIDON VA 64, KOLLIDON K-30, and KOLLIDON CL-M (all available from KAWARLAL); and KOLLICOAT IR (available from BASF). These may be used alone or in combination.

The polyvinyl alcohol is not particularly limited and may be appropriately selected depending on the intended purpose. Examples of the polyvinyl alcohol include silanol-modified polyvinyl alcohol, carboxyl-modified polyvinyl alcohol, and acetoacetyl-modified polyvinyl alcohol. These may be used alone or in combination.

The polyvinyl acetate is not particularly limited and may be appropriately selected depending on the intended purpose. Examples of the polyvinyl acetate include vinyl acetate/crotonic acid copolymers and vinyl acetate/itaconic acid copolymers. These may be used alone or in combination.

The biodegradable polyesters are not particularly limited and may be appropriately selected depending on the intended purpose. Examples of the biodegradable polyesters include polylactic acid, poly-epsilon-caprolactone, succinate-based polymers, and polyhydroxy alkanoate. These may be used alone or in combination.

The succinate-based polymers are not particularly limited and may be appropriately selected depending on the intended purpose. Examples of the succinate-based polymers include polyethylene succinate, polybutylene succinate, and polybutylene succinate adipate. These may be used alone or in combination.

The polyhydroxy alkanoate is not particularly limited and may be appropriately selected depending on the intended purpose. Examples of the polyhydroxy alkanoate include polyhydroxy propionate, polyhydroxy butyrate, and polyhydroxy barylate. These may be used alone or in combination.

The polyglycolic acids are not particularly limited and may be appropriately selected depending on the intended purpose. Examples of the polyglycolic acids include lactic acid-glycolic acid copolymers, glycolic acid-caprolactone copolymers, and glycolic acid-trimethylene carbonate copolymers. These may be used alone or in combination.

The polyamino acids are not particularly limited and may be appropriately selected depending on the intended purpose. Examples of the polyamino acids include homopolymers of amino acids such as poly-alpha-glutamic acid, poly-gamma-glutamic acid, polyaspartic acid, polylysine, polyarginine, polyornithine, and polyserine; or copolymers of the above-described amino acids. These may be used alone or in combination.

The gelatin is not particularly limited and may be appropriately selected depending on the intended purpose. Examples of the gelatin include alkali processed gelatin, acid processed gelatin, gelatin hydrolysate, enzymatically dispersed gelatin, or derivatives of the above-described gelatins. These may be used alone or in combination.

Natural polymeric dispersing agents used for the gelatin derivatives are not particularly limited and may be appropriately selected depending on the intended purpose. Examples of the natural polymeric dispersing agents include proteins, polysaccharides, and nucleic acids. These may be used alone or in combination. These include the natural polymeric dispersing agents or copolymers including synthetic polymeric dispersing agents.

The gelatin derivatives refer to gelatins derivatized by covalently binding hydrophobic groups to gelatin molecules. The hydrophobic groups are not particularly limited and may be appropriately selected depending on the intended purpose. Examples of the hydrophobic groups include polyesters such as polylactic acid, polyglycolic acid, and poly-epsilon-caprolactone; lipids such as cholesterol and phosphatidyl ethanolamine; aromatic groups including alkyl groups and benzene rings; heterocyclic aromatic groups; or mixture of the above-described hydrophobic group.

The proteins are not particularly limited and may be appropriately selected depending on the intended purpose.

Examples of the proteins include collagen, fibrin, and albumin. These may be used alone or in combination.

The polysaccharides are not particularly limited and may be appropriately selected depending on the intended purpose. Examples of the polysaccharides include chitin, chitosan, hyaluronic acid, alginic acid, starches, and pectin. These may be used alone or in combination.

An amount of the dispersing agent is preferably 5% by mass or more but 95% by mass or less, more preferably 50% by mass or more but 95% by mass or less relative to the total amount of the particles of the present invention. The amount of 5% by mass or more but 95% by mass or less is advantageous in that the dispersing agent is administered at a dosage appropriate as a pharmaceutical composition and a pharmaceutical component is easily redispersed in water by the action of the dispersing agent.

-Solvent-

The solvent is not particularly limited and may be appropriately selected depending on the intended purpose, but is preferably those into which the poorly water-soluble compounds or pharmaceutically acceptable salts of the poorly water-soluble compounds are dissolvable or dispersible.

Examples of the solvent include aliphatic halogenated hydrocarbons (e.g., dichloromethane, dichloroethane, and chloroform), alcohols (e.g., methanol, ethanol, and propanol), ketones (e.g., acetone and methylethylketone), ethers (e.g., diethyl ether, dibutyl ether, and 1,4-dioxane), aliphatic hydrocarbons (e.g., n-hexane, cyclohexane, and n-heptane), aromatic hydrocarbons (e.g., benzene, toluene, and xylene), organic acids (e.g., acetic acid and propionic acid), esters (e.g., ethyl acetate), amides (e.g., dimethylformamide and dimethylacetamide), or mixed solvents of the above-described solvents. These may be used alone or in combination. Among them, aliphatic halogenated hydrocarbons, alcohols, or mixed solvents of the above-described solvents are preferable, and dichloromethane, 1,4-dioxane, methanol, ethanol, or mixed solvents of the above-described solvents are more preferable from the viewpoint of solubility.

An amount of the solvent is preferably 70% by mass or more but 99.5% by mass or less, more preferably 90% by mass or more but 99% by mass or less relative to the total amount of the particles of the present invention. The amount of 70% by mass or more but 99.5% by mass or less is advantageous from the viewpoint of production stability in terms of solubility and solution viscosity of materials.

-Other Components-

The other components are not particularly limited and may be appropriately selected depending on the intended purpose, but are preferably those being pharmaceutically known and usable.

Examples of the other components include water, excipients, taste masking agents, disintegrating agents, fluidizers, adsorbing agents, lubricants, odor masking agents, surfactants, flavoring agent, colorants, anti-oxidants, masking agents, anti-static agents, and humectants. These may be used alone or in combination.

The excipients are not particularly limited and may be appropriately selected depending on the intended purpose. Examples of the excipients include lactose, sucrose, mannitol, glucose, fructose, maltose, erythritol, maltitol, xylitol, palatinose, trehalose, sorbitol, microcrystalline cellulose, talc, silica, anhydrous calcium phosphate, precipitated calcium carbonate, and calcium silicate. These may be used alone or in combination.

The taste masking agents are not particularly limited and may be appropriately selected depending on the intended purpose. Examples of the taste masking agents include L-menthol, refined sugar, D-sorbitol, xylitol, citric acid, ascorbic acid, tartaric acid, malic acid, aspartame, acesulfame potassium, thaumatin, saccharin sodium, dipotassium glycyrrhizinate, sodium glutamate, sodium 5'-inosinate, and sodium 5'-guanylate. These may be used alone or in combination.

The disintegrating agents are not particularly limited and may be appropriately selected depending on the intended purpose. Examples of the disintegrating agents include hydroxypropyl celluloses with a low substitution degree, carmellose, carmellose calcium, carboxymethyl starch sodium, croscarmellose sodium, crospovidone, hydroxypropyl starch, and corn starch. These may be used alone or in combination.

The fluidizers are not particularly limited and may be appropriately selected depending on the intended purpose. Examples of the fluidizers include light anhydrous silicic acid, hydrated silicon dioxide, and talc. These may be used alone or in combination.

The light anhydrous silicic acid may be commercially available products. The commercially available products are not particularly limited and may be appropriately selected depending on the intended purpose. Examples of the commercially available products include ADSOLIDER 101 (available from Freund Corporation: average pore diameter: 21 nm).

The adsorbing agents may be commercially available products. The commercially available products are not particularly limited and may be appropriately selected depending on the intended purpose. Examples of the commercially available products include product name: CARPLEX (component name: synthetic silica, registered trademark of DSL. Japan Co., Ltd.), product name: AEROSIL (registered trademark of NIPPON AEROSIL CO., LTD.) 200 (component name: hydrophilic fumed silica), product name: SYLYSIA (component name: amorphous silicon dioxide, registered trademark of Fuji Silysia Chemical Ltd), and product name: ALCAMAC (component name: synthetic hydrotalcite, registered trademark of Kyowa Chemical Industry Co., Ltd.). These may be used alone or in combination.

The lubricants are not particularly limited and may be appropriately selected depending on the intended purpose. Examples of the lubricants include magnesium stearate, calcium stearate, sucrose fatty acid ester, sodium stearyl fumarate, stearic acid, polyethylene glycol, and talc. These may be used alone or in combination.

The odor masking agents are not particularly limited and may be appropriately selected depending on the intended purpose. Examples of the odor masking agents include trehalose, malic acid, maltose, potassium gluconate, aniseed essential oil, vanilla essential oil, and cardamom oil. These may be used alone or in combination.

The surfactants are not particularly limited and may be appropriately selected depending on the intended purpose. Examples of the surfactants include polysorbates such as polysorbate 80; polyoxyethylene-polyoxypropylene copolymers; and sodium lauryl sulfate. These may be used alone or in combination.

The flavoring agents are not particularly limited and may be appropriately selected depending on the intended purpose. Examples of the flavoring agents include lemon oils, orange oils, and peppermint oils. These may be used alone or in combination.

The colorants are not particularly limited and may be appropriately selected depending on the intended purpose. Examples of the colorants include titanium oxide, Food Yellow No. 5, Food Blue No. 2, iron sesquioxide, and yellow iron sesquioxide. These may be used alone or in combination.

The anti-oxidants are not particularly limited and may be appropriately selected depending on the intended purpose. Examples of the anti-oxidants include sodium ascorbate, L-cysteine, sodium sulfite, vitamin E. These may be used alone or in combination.

The masking agents are not particularly limited and may be appropriately selected depending on the intended purpose. Examples of the masking agents include titanium oxide. These may be used alone or in combination.

The anti-static agents are not particularly limited and may be appropriately selected depending on the intended purpose. Examples of the anti-static agents include talc and titanium oxide. These may be used alone or in combination.

The humectants are not particularly limited and may be appropriately selected depending on the intended purpose. Examples of the humectants include polysorbate 80, sodium lauryl sulfate, sucrose fatty acid ester, macrogol, and hydroxypropyl cellulose (HPC). These may be used alone or in combination.

An amount of the other components is preferably 1% by mass or more but 10% by mass or less, more preferably 1% by mass or more but 5% by mass or less relative to the total amount of the particles of the present invention. The amount of 1% by mass or more but 10% by mass or less is advantageous in that redispersibility with the dispersing agent is not impaired and homogeneity is less problematic.

A viscosity of the liquid is not particularly limited and may be appropriately selected depending on the intended purpose, but is preferably 0.5 mPa·s or more but 15.0 mPa·s or less, more preferably 0.5 mPa·s or more but 10.0 mPa·s or less. Note that, the viscosity may be measured using a viscoelasticity measurement device (device name: MCR rheometer, available from AntonPaar) under the conditions of 25 degrees Celsius and a shear rate of 10 $s^{-1}$.

A surface tension of the liquid is not particularly limited and may be appropriately selected depending on the intended purpose, but is preferably 10 mN/m or more but 60 mN/m or less, more preferably 20 mN/m or more but 50 mN/m or less. Note that, the surface tension may be measured by a maximum foaming pressure method using, for example, a portable surface tensiometer (device name: POCKETDYNE, available from KRUSS) under the conditions of 25 degrees Celsius and a lifetime of 1,000 ms.

The liquid may include no solvent, provided that the physiologically active substance is dissolved, the physiologically active substance is dispersed, or the physiologically active substance is in the liquid state under conditions under which the liquid is discharged. Alternatively, particle components may be melted.

<Method for Preparing Liquid>

A method for preparing the liquid is not particularly limited and may be appropriately selected depending on the intended purpose. Examples of the method include (i) a method in which the physiologically active substance is added to the solvent along with the dispersing agent and then mixed and stirred in a planetary centrifugal mixer (available from THINKY CORPORATION) with zirconia beads in a range of from 0.03 mm through 10 mm at 100 rpm or more but 5,000 rpm or less for from several minutes to several hours to thereby be dispersed; and (ii) a method in which the physiologically active substance is added to the solvent along with the dispersing agent and then mixed and stirred in a stirrer (device name: magnetic stirrer, available from AS ONE Corporation) at 1,000 rpm for 1 hour to thereby be dispersed.

<<Discharging Port>>

The discharging port is not particularly limited and may be appropriately selected depending on the intended purpose. For example, the discharging port is an outlet of an opening of a discharging hole disposed, for example, on a nozzle plate. For example, a plurality of the discharging ports are disposed on the nozzle plate.

The number of the discharging ports is not particularly limited and may be appropriately selected depending on the intended purpose, but is preferably 2 or more but 3,000 or less. When the number of the discharging ports is 2 or more but 3,000 or less, productivity is capable of being improved.

A diameter of the discharging ports is not particularly limited and may be appropriately selected depending on the intended purpose, but is preferably 1 micrometer or more but 40 micrometers or less, more preferably 6 micrometers or more but 40 micrometers or less. When the diameter is 1 micrometer or more, the resultant liquid droplets may be prevented from being very small and particles may be more easily obtained. Even when solid particles such as pigments are included in the particles, the discharge ports may be prevented from frequently clogging, the clogging leading to decreased productivity. When the diameter is 40 micrometers or less, the resultant liquid droplets may be prevented from having a large diameter. When the resultant liquid droplets are dried to obtain particles having a desired particle diameter of 3 micrometers or more but 6 micrometers or less, a particle composition is not needed to be diluted to a very thin solution with a solvent. As a result, it is prevented that a large amount of drying energy is needed to obtain a certain amount of the particles.

A cross-sectional shape of the discharging port is not particularly limited and may be appropriately selected depending on the intended purpose. Examples of the cross-sectional shape include (1) a tapered shape in which an opening diameter gradually decreases from a liquid-contacting surface (inlet) towards a discharging port (outlet) of a discharge hole; (2) a shape in which an opening diameter gradually decreases from a liquid-contacting surface (inlet) towards a discharging port (outlet) of a discharge hole while keeping a rounded shape; (3) a shape in which an opening diameter gradually decreases from a liquid-contacting surface (inlet) towards a discharging port (outlet) of a discharge hole at a constant nozzle angle; and (4) a combination of the shape in (1) with the shape in (2). Among them, (3) the shape in which an opening diameter gradually decreases from a liquid-contacting surface (inlet) towards a discharging port (outlet) of a discharge hole at a constant nozzle angle is preferable because pressure applied to the liquid at the discharging port is the largest.

The nozzle angle in the case of (3) is not particularly limited and may be appropriately selected depending on the intended purpose, but 60 degrees or more but 90 degrees or less. When the nozzle angle is 60 degrees or more, pressure is more likely to be applied to the liquid, resulting in easy processing. When the nozzle angle is 90 degrees or less, pressure is applied at the discharging port, resulting in stable discharging of the liquid droplets. Therefore, the nozzle angle is preferably at most 90 degrees.

<<Liquid-Column Resonance Method>>

A method for discharging liquid droplets in the method for producing particles of the present invention may be a liquid-column resonance method or other methods.

The other methods are not particularly limited and may be appropriately selected depending on the intended purpose. Examples of the other methods include membrane-vibration methods, liquid-vibration methods, Rayleigh-breakup methods, and thermal methods.

The liquid-column resonance method is superior to the membrane-vibration methods or the liquid-vibration methods from the viewpoints of no occurrence of cavitation and continuous productivity. The liquid-column resonance method is superior to the Rayleigh-breakup methods from the viewpoints of dischargeability, continuous productivity, and production stability. Moreover, the liquid-column resonance method is superior to the thermal methods because appropriate materials are not limited due to no application of heat and continuous productivity is more excellent.

The liquid-column resonance method is not particularly limited and may be appropriately selected depending on the intended purpose. For example, the liquid-column resonance method includes applying vibration to a liquid including a physiologically active substance and included in a liquid-column resonance liquid-chamber to form a standing wave based on liquid column resonance, to thereby discharge the liquid from at least one discharging port, which is formed in an amplitude direction of the standing wave, to at least one region corresponding to at least one anti-node of the standing wave.

The liquid-column resonance method may be suitably performed by a liquid-column resonance liquid-droplet discharging section.

The liquid-column resonance liquid-droplet discharging section will now be described below.

FIG. 1 is a schematic, cross-sectional view illustrating a liquid-column resonance liquid-droplet discharging section 11. The liquid-column resonance liquid-droplet discharging section 11 includes a common liquid supplying-path 17 and a liquid-column resonance liquid-chamber 18. The liquid-column resonance liquid-chamber 18 is in communication with the common liquid supplying-path 17 disposed on one of wall surfaces at both ends in a longitudinal direction. The liquid-column resonance liquid-chamber 18 includes discharging ports 19 and a vibration generating section 20. The discharging ports 19 are disposed on one of wall surfaces that are coupled to the wall surfaces at the both ends and are configured to discharge liquid droplets 21. The vibration generating section 20 is disposed at a wall surface opposite to the wall surface on which the discharging ports 19 are disposed and is configured to generate high frequency vibration in order to form a liquid-column resonance standing wave. Note that, a high-frequency power-source (not illustrated) is coupled to the vibration generating section 20.

FIG. 2 is a cross-sectional view illustrating one exemplary liquid-column resonance liquid-droplet discharging unit. A liquid 14 is supplied into the common liquid supplying-path 17 of a liquid-column resonance liquid-droplet forming unit 10 illustrated in FIG. 2 through a liquid supplying pipe by a liquid circulating pump (not illustrated). Then, the liquid 14 is supplied into the liquid-column resonance liquid-chamber 18 of the liquid-column resonance liquid-droplet discharging section 11 illustrated in FIG. 1. In the liquid-column resonance liquid-chamber 18 filled with the liquid 14, a pressure distribution is formed by the action of a liquid-column resonance standing-wave generated by the vibration generating section 20. Then, the liquid droplets 21 are discharged from the discharge ports 19 which are disposed in regions corresponding to anti-nodes, where an amplitude and pressure fluctuation are large, of the liquid-column resonance standing-wave. The anti-nodes of the liquid-column resonance standing-wave refer to other regions than nodes of the standing wave. The anti-nodes are preferably regions in which the pressure fluctuation of the standing wave has a large amplitude enough to discharge the liquid, and more preferably regions having a width corresponding to ±¼ of a wavelength from a position of a local maximum amplitude of a pressure standing wave (i.e., a node of a velocity standing wave) toward positions of a local minimum amplitude.

Even when a plurality of discharge ports are opened, substantially uniform liquid droplets are capable of being formed from the plurality of discharge ports so long as the discharge ports are disposed in the regions corresponding to the anti-nodes of the standing wave. Moreover, the liquid droplets are capable of being discharged efficiently, and the discharge ports are less likely to be clogged. Note that, the liquid 14 which has flowed through the common liquid supplying-path 17 is returned to a raw-material container via a liquid returning pipe (not illustrated). When the liquid droplets 21 are discharged to decrease an amount of the liquid 14 in the liquid-column resonance liquid-chamber 18, a larger amount of the liquid 14 is supplied from the common liquid supplying-path 17 by suction power generated by the action of the liquid-column resonance standing-wave in the liquid-column resonance liquid-chamber 18. As a result, the liquid-column resonance liquid-chamber 18 is refilled with the liquid 14. When the liquid-column resonance liquid-chamber 18 is refilled with the liquid 14, an amount of the liquid 14 flowing through the common liquid supplying-path 17 returns to as before.

The liquid-column resonance liquid-chamber 18 of the liquid-column resonance liquid-droplet discharging section 11 is formed by joining frames with each other. The frames are formed of materials having high stiffness to the extent that a liquid resonance frequency is not influenced at a driving frequency (e.g., metals, ceramics, and silicones). As illustrated in FIG. 1, a length L between the wall surfaces at the both ends of the liquid-column resonance liquid-chamber 18 in a longitudinal direction is determined based on the principle of the liquid column resonance described below. A width W of the liquid-column resonance liquid-chamber 18 illustrated in FIG. 2 is preferably shorter than ½ of the length L of the liquid-column resonance liquid-chamber 18 so as not to add any frequency unnecessary for the liquid column resonance. A plurality of the liquid-column resonance liquid-chambers 18 are preferably disposed per one liquid-droplet forming unit 10 in order to drastically improve productivity. The number of the liquid-column resonance liquid-chambers 18 is not particularly limited and may be appropriately selected depending on the intended purpose, but is preferably 100 or more but 2,000 or less because both of operability and productivity are capable of being achieved. The common liquid supplying-path 17 is coupled to and in communication with a liquid supplying-path for each liquid-column resonance liquid-chamber. The common liquid supplying-path 17 is in communication with a plurality of the liquid-column resonance liquid-chambers 18.

The vibration generating section 20 of the liquid-column resonance liquid-droplet discharging section 11 is not particularly limited, so long as the vibration generating section is capable of being driven at a predetermined frequency. However, the vibration generating section is preferably formed by attaching a piezoelectric material onto an elastic plate 9. The frequency is preferably 150 kHz or more, more preferably 300 kHz or more but 500 kHz or less from the viewpoint of productivity. The elastic plate constitutes a portion of the wall of the liquid-column resonance liquid-chamber so as not to contact the piezoelectric material with the liquid. The piezoelectric material may be, for example, piezoelectric ceramics such as lead zirconate titanate (PZT), and is typically often laminated due to a small displacement amount. Other examples of the piezoelectric material include piezoelectric polymers (e.g., polyvinylidene fluoride (PVDF)) and monocrystals (e.g., crystal, $LiNbO_3$, $LiTaO_3$, and $KNbO_3$). The vibration generating section 20 is preferably disposed so as to be individually controlled for each liquid-column resonance liquid-chamber. It is preferable that the liquid-column resonance liquid-chambers are capable of being individually controlled via the elastic plates by partially cutting a block-shaped vibration member, which is formed of one of the above-described materials, according to geometry of the liquid-column resonance liquid-chambers.

As can be seen from FIG. 2, the discharge ports 19 are preferably disposed in a width direction of the liquid-column resonance liquid-chamber 18 because many discharge ports 19 are capable of being disposed to improve production efficiency. Additionally, it is preferable that a liquid-column resonance frequency be determined appropriately after verifying how the liquid droplets are discharged because the liquid-column resonance frequency varies depending on arrangement of the discharge ports 19.

FIGS. 3A to 3D are schematic views illustrating exemplary structures of discharging holes. In FIGS. 3A to 3D, cross-sectional shapes of the discharging holes are illustrated as tapered shapes in which opening diameters gradually decrease from liquid-contacting surfaces (inlet) towards discharging ports (outlet) of the discharge holes. However, the cross-sectional shapes may be appropriately selected.

In FIG. 3A, the discharging holes have a shape in which an opening diameter gradually decreases from a liquid-contacting surface towards the discharging port 19 of the discharge hole while keeping a rounded shape. This shape is the most preferable from the viewpoint of stable discharging because pressure applied to the liquid at the discharging port is the largest.

In FIG. 3B, the discharging holes have a shape in which an opening diameter gradually decreases from a liquid-contacting surface towards a discharging port 19 of the discharge hole at a constant angle. This nozzle angle 24 is capable of being changed appropriately. It is possible to increase pressure applied to the liquid adjacent to the discharging holes depending on the nozzle angle, like the shape illustrated in FIG. 3A. The nozzle angle 24 is not particularly limited and may be appropriately selected depending on the intended purpose, but 60 degrees or more but 90 degrees or less. When the nozzle angle is 60 degrees or more, pressure is more likely to be applied to the liquid, resulting in easy processing. When the nozzle angle 24 is 90 degrees or less, pressure is applied adjacent to the outlets of the discharging holes, resulting in stable discharging of the liquid droplets. Therefore, the nozzle angle 24 is preferably at most 90 degrees (corresponding to FIG. 3C).

In FIG. 3D, the discharging holes have a combined shape of the shape illustrated in FIG. 3A with the shape illustrated in FIG. 3B. The shape of the discharging holes may be varied stepwise in this way.

A mechanism by which liquid droplets are formed by the liquid-droplet forming unit based on the liquid column resonance will now be described.

Firstly, the principle of a liquid-column resonance phenomenon that occurs in the liquid-column resonance liquid-chamber 18 of the liquid-column resonance liquid-droplet discharging section 11 illustrated in FIG. 1 will now be described.

A wavelength (Lambda) at which liquid resonance occurs is represented by Expression 1 below:

$$Lambda = c/f \quad \text{(Expression 1)}$$

where c denotes sound velocity of the liquid in the liquid-column resonance liquid-chamber; and f denotes a driving frequency applied by the vibration generating section 20 to the liquid serving as a medium.

In the liquid-column resonance liquid-chamber 18 in FIG. 1, a length from a frame end at a fixed end side to an end at the common liquid supplying-path 17 side is represented as L. A height h1 (about 80 micrometers) of the frame end at the common liquid supplying-path 17 side is about 2 times as high as a height h2 (about 40 micrometers) of a communication port. The end at the common liquid supplying-path side is assumed to be equivalent to a closed fixed end. In such cases where both ends are fixed, resonance is most efficiently formed when the length L corresponds to an even multiple of ¼ of the wavelength (Lambda). This is capable of being represented by Expression 2 below:

$$L = (N/4)Lambda \quad \text{(Expression 2)}$$

In the Expression 2, L denotes a length of the liquid-column resonance liquid-chamber in a longitudinal direction; N denotes an even number; and Lambda denotes a wavelength at which liquid resonance occurs.

The Expression 2 is also satisfied when the both ends are free, that is, the both ends are completely opened.

Likewise, when one end is equivalent to a free end from which pressure is released and the other end is closed (fixed end), that is, when one of the ends is fixed or one of the ends is free, resonance is most efficiently formed when the length L corresponds to an odd multiple of ¼ of the wavelength Lambda. That is, N in the Expression 2 denotes an odd number.

The most efficient driving frequency f is represented by Expression 3 which is derived from the Expression 1 and the Expression 2:

$$f = N \times c/(4L) \quad \text{(Expression 3)}$$

In the Expression 3, L denotes a length of the liquid-column resonance liquid-chamber in a longitudinal direction; c denotes velocity of an acoustic wave of a liquid; and N denotes a natural number.

However, actually, vibration is not amplified unlimitedly because liquid has viscosity which attenuates resonance. Therefore, the resonance has a Q factor, and also occurs at a frequency adjacent to the most efficient driving frequency f calculated according to the Expression 3, as represented by Expression 4 and Expression 5 below.

FIG. 4A is a schematic view illustrating a standing wave of velocity fluctuation and a standing wave of pressure fluctuation when $N=1$ and one end is fixed. FIG. 4B is a schematic view illustrating a standing wave of velocity fluctuation and a standing wave of pressure fluctuation when $N=2$ and both ends are fixed. FIG. 4C is a schematic view illustrating a standing wave of velocity fluctuation and a standing wave of pressure fluctuation when $N=2$ and both ends are free. FIG. 4D is a schematic view illustrating a standing wave of velocity fluctuation and a standing wave of pressure fluctuation when $N=3$ and one end is fixed. FIG. 5A is a schematic view illustrating a standing wave of velocity fluctuation and a standing wave of pressure fluctuation when N=4 and both ends are fixed. FIG. 5B is a schematic view illustrating a standing wave of velocity fluctuation and a standing wave of pressure fluctuation when N=4 and both ends are free. FIG. 5C is a schematic view illustrating a standing wave of velocity fluctuation and a standing wave of pressure fluctuation when N=5 and one end is fixed.

In FIGS. 4A to 4D and 5A to 5C, a solid line represents a velocity distribution and a dotted line represents a pressure distribution. Standing wave are actually compressional waves (longitudinal waves), but are commonly expressed as illustrated in FIGS. 4A to 4D and 5A to 5C. A solid line represents a velocity standing wave and a dotted line represents a pressure standing wave. For example, as can be seen from FIG. 4A in which N=1 and one end is fixed, an amplitude of the velocity distribution is zero at a closed end and the maximum at an opened end, which is understandable intuitively. Assuming that a length between both ends of the liquid-column resonance liquid-chamber in a longitudinal direction is L and a wavelength at which liquid column resonance of liquid occurs is Lambda, the standing wave is most efficiently generated when the integer N is from 1 through 5. A standing wave pattern varies depending on whether each end is opened or closed. Therefore, standing wave patterns under various opening/closing conditions are also described in the drawings. As described below, conditions of the ends are determined depending on states of openings of the discharge ports and states of openings at a supplying side.

Note that, in the acoustics, an opened end refers to an end at which moving velocity of a medium reaches the local maximum, but, to the contrary, pressure of the medium is zero. Conversely, a closed end refers to an end at which moving velocity of a medium (liquid) is zero in a longitudinal direction, but, to the contrary, pressure of the medium reaches the local maximum. The closed end is considered as an acoustically hard wall and reflects a wave. When an end is ideally perfectly closed or opened, resonance standing waves as illustrated in FIGS. 4A to 4D and 5A to 5C are formed by superposition of waves. However, standing wave patterns vary depending on the number of the discharge ports and positions at which the discharge ports are opened. Therefore, a resonance frequency appears at a position shifted from a position determined according to the Expression 3. In this case, stable discharging conditions are capable of being created by appropriately adjusting the driving frequency. For example, when the sound velocity c of the liquid is 1,200 m/s, the length L of the liquid-column resonance liquid-chamber is 1.85 mm, and a resonance mode in which both ends are completely equivalent to fixed ends due to the presence of walls on the both ends and N=2 is used, the most efficient resonance frequency is calculated as 324 kHz from the Expression 2. In another example, when the sound velocity c of the liquid is 1,200 m/s and the length L of the liquid-column resonance liquid-chamber is 1.85 mm, these conditions being the same as above, and a resonance mode in which both ends are equivalent to fixed ends due to the presence of walls at the both ends and N=4 is used, the most efficient resonance frequency is calculated as 648 kHz from the Expression 2. Thus, a higher-order resonance is capable of being utilized even in a liquid-column resonance liquid-chamber having the same configuration.

In order to increase the frequency, the liquid-column resonance liquid-chamber of the liquid-column resonance liquid-droplet discharging section 11 illustrated in FIG. 1 preferably has both ends which are equivalent to a closed end or are considered as an acoustically soft wall due to influence from openings of the discharge ports. However, the both ends may be free. The influence from openings of the discharge ports means decreased acoustic impedance and, in particular, an increased compliance component. Therefore, the configuration in which walls are formed at both ends of the liquid-column resonance liquid-chamber in a longitudinal direction, as illustrated in FIGS. 4B and 5A, is preferable because both of a resonance mode in which both ends are fixed and a resonance mode in which one of ends is free, that is, an end at a discharge port side is considered to be opened are capable of being used.

The number of openings of the discharge ports, positions at which the openings are disposed, and cross-sectional shapes of the discharge ports are also factors which determine the driving frequency. The driving frequency is capable of being appropriately determined based on these factors. For example, when the number of the discharge ports is increased, the liquid-column resonance liquid-chamber gradually becomes free at an end which has been fixed. As a result, a resonance standing wave which is approximately the same as a standing wave at the opened end is generated and the driving frequency is increased. Further, the end which has been fixed becomes free starting from a position at which an opening of the discharge port that is the closest to the liquid supplying-path is disposed. As a result, a cross-sectional shape of the discharge port is changed to a rounded shape or a volume of the discharge port is varied depending on a thickness of the frame, so that an actual standing wave has a shorter wavelength and a higher frequency than the driving frequency. When a voltage is applied to the vibration generating section at the driving frequency determined as described above, the vibration generating section deforms and the resonance standing wave is generated most efficiently at the driving frequency. The liquid-column resonance standing-wave is also generated at a frequency adjacent to the driving frequency at which the resonance standing wave is generated most efficiently. That is, assuming that a length between both ends of the liquid-column resonance liquid-chamber in a longitudinal direction is L and a distance to a discharge port that is the closest to an end at a liquid supplying side is Le, the driving frequency f is determined according to Expression 4 and Expression 5 below using both of the lengths L and Le. A driving waveform having, as a main component, the driving frequency f is capable of being used to vibrate the vibration generating section and induce the liquid column resonance to thereby discharge the liquid droplets from the discharge ports.

$$N \times c/(4L) \leq f \leq N \times c/(4Le) \quad \text{(Expression 4)}$$

$$N \times c/(4L) \leq f \leq (N+1) \times c/(4Le) \quad \text{(Expression 5)}$$

In the Expressions 4 and 5, L denotes a length of the liquid-column resonance liquid-chamber in a longitudinal direction; Le denotes a distance from an end at a liquid supplying-path side to a center of a discharging hole that is the closest to the end; c denotes velocity of an acoustic wave of a liquid; and N denotes a natural number.

Note that, a ratio of the length L between both ends of the liquid-column resonance liquid-chamber in a longitudinal direction to the distance Le to the discharge port that is the closest to the end at the liquid supplying side (Le/L) preferably satisfies Expression 6 below.

$$Le/L > 0.6 \quad \text{(Expression 6)}.$$

Based on the principle of the liquid-column resonance phenomenon described above, a liquid-column resonance pressure standing-wave is formed in the liquid-column resonance liquid-chamber 18 illustrated in FIG. 1, and the liquid droplet are continuously discharged from the discharge ports 19 disposed in a portion of the liquid-column resonance liquid-chamber 18. Note that, the discharge port 19 is preferably disposed at a position at which pressure of the standing wave vary to the greatest extent from the viewpoints of high discharging efficiency and driving at a lower voltage. One liquid-column resonance liquid-chamber 18 may include one discharge port 19, but preferably includes two or more (a plurality of) discharge ports from the viewpoint of productivity. Specifically, the number of discharge ports is preferably 2 or more but 100 or less. When the number of discharge ports is 2 or more, improved productivity is capable of being achieved. When the number of discharge ports is 100 or less, a voltage to be applied to the vibration generating section 20 may be set at a low level in order to form desired liquid droplets from the discharge ports 19. As a result, a piezoelectric material stably behaves as the vibration generating section 20.

When the plurality of the discharge ports 19 are disposed, a pitch between the discharge ports (the shortest distance between centers of discharging holes adjacent to each other) is preferably 20 micrometers or longer but equal to or shorter than the length of the liquid-column resonance liquid-chamber. When the pitch between the discharge ports is 20 micrometers or more, the possibility that liquid droplets, which are discharged from discharge ports adjacent to each other, collide with each other to form a larger droplet is capable of being decreased. As a result, particles having a good particle diameter distribution may be obtained.

Next, a liquid column resonance phenomenon which occurs in the liquid-column resonance liquid-chamber of a liquid-droplet discharging head of the liquid-droplet forming unit will be described referring to FIGS. 6A to 6E. Note that, in FIGS. 6A to 6E, a solid line drawn in the liquid-column resonance liquid-chamber represents a velocity distribution plotting velocity at arbitrary measuring positions between an end at the fixed end side and an end at the common liquid supplying-path side in the liquid-column resonance liquid-chamber. A direction from the common liquid supplying-path to the liquid-column resonance liquid-chamber is assumed as plus (+), and the opposite direction is assumed as minus (−). A dotted line drawn in the liquid-column resonance liquid-chamber represents a pressure distribution plotting pressure at arbitrary measuring positions between an end at the fixed end side and an end at the common liquid supplying-path side in the liquid-column resonance liquid-chamber. A positive pressure relative to atmospheric pressure is assumed as plus (+), and a negative pressure is assumed as minus (−). In the case of the positive pressure, pressure is applied in a downward direction in the drawings. In the case of the negative pressure, pressure is applied in an upward direction in the drawings. In FIGS. 6A to 6E, as described above, the end at the common liquid supplying-path side is free, and the height of the frame serving as the fixed end (height h1 in FIG. 1) is about 2 times or more as high as the height of an opening at which the common liquid supplying-path 17 is in communication with the liquid-column resonance liquid-chamber 18 (height h2 in FIG. 1). Therefore, FIGS. 6A to 6E represent temporal changes of a velocity distribution and a pressure distribution under an approximate condition in which the liquid-column resonance liquid-chamber 18 are approximately fixed at both ends. In FIGS. 6A to 6E, a solid line represents a velocity distribution and a dotted line represents a pressure distribution.

A schematic view illustrating another exemplary liquid-column resonance phenomenon occurred in a liquid-column resonance flow path of a liquid-column resonance liquid-droplet discharging section.

FIG. 6A illustrates a pressure waveform and a velocity waveform in the liquid-column resonance liquid-chamber 18 at a time when liquid droplets are discharged. In FIG. 6B, meniscus pressure is increased again after the liquid droplets are discharged and immediately then the liquid is drawn. As illustrated in FIGS. 6A and 6B, pressure in a flow path, on which the discharge ports 19 are disposed, in the liquid-column resonance liquid-chamber 18 is the local maximum. Then, as illustrated in FIG. 6C, positive pressure adjacent to the discharge ports 19 is decreased and shifted to a negative pressure side. Thus, the liquid droplets 21 are discharged.

Then, as illustrated in FIG. 6D, the pressure adjacent to the discharge ports 19 is the local minimum. From this time point, the liquid-column resonance liquid-chamber 18 starts to be filled with the liquid 14. Then, as illustrated in FIG. 6E, negative pressure adjacent to the discharge ports 19 is decreased and shifted to a positive pressure side. At this time point, the liquid chamber is completely filled with the liquid 14. Then, as illustrated in FIG. 6A, positive pressure in a liquid-droplet discharging region of the liquid-column resonance liquid-chamber 18 is the local maximum again to discharge the liquid droplets 21 from the discharge ports 19. Thus, the liquid-column resonance standing-wave is generated in the liquid-column resonance liquid-chamber by the vibration generating section driven at a high frequency. The discharge ports 19 are disposed in the liquid-droplet discharging region corresponding to the anti-nodes of the liquid-column resonance standing-wave at which pressure varies to the greatest extent. Therefore, the liquid droplets 21 are continuously discharged from the discharge ports 19 in synchronized with an appearance cycle of the anti-nodes.

One exemplary aspect where liquid droplets are actually discharged based on the liquid column resonance phenomenon will now be described. FIG. 7 is an image illustrating exemplary actual liquid droplets discharged by a liquid-column resonance liquid-droplet discharging section. In this example, liquid droplets were discharged under the below-described conditions: the length L between both ends of the liquid-column resonance liquid-chamber 18 in a longitudinal direction in FIG. 1 was 1.85 mm, a resonance mode was N=2, the first to fourth discharge ports were disposed at positions corresponding to anti-nodes of a pressure standing wave in the resonance mode of N=2, and the drive frequency was a sine wave at 340 kHz. FIG. 7 is a photograph of the thus-discharged liquid droplets, the photograph was taken by laser shadowgraphy. As can be seen from FIG. 7, the liquid droplets which are very uniform in diameter and substantially uniform in velocity were successfully discharged.

FIG. 8 is a graph illustrating dependency of a liquid-droplet discharging velocity on a driving frequency when driven by a sine wave having the same amplitude of 290 kHz or more but 395 kHz or less as the drive frequency. As can be seen from FIG. 8, a discharge velocity of liquid droplets from each of the first to fourth discharge nozzles is uniform and the highest adjacent to the drive frequency of about 340 kHz. It can be seen from this result that liquid droplets are uniformly discharged at a position corresponding to an anti-node of the liquid column resonance standing wave at 340 kHz which is the second mode of a liquid column resonance frequency. It can also be seed from the results in FIG. 8 that a frequency characteristic of liquid column resonance standing waves characteristic of the liquid column resonance occurs in the liquid-column resonance liquid-chamber. The frequency characteristic is that liquid droplets are not discharged between a liquid-droplet discharging velocity peak at 130 kHz, which is the first mode, and a liquid-droplet discharging velocity peak at 340 kHz, which is the second mode.

<Particle Forming Step>

The particle forming step is a step of drying discharged liquid to form particles.

In the particle forming step, the liquid discharged into a gas in the discharging step is capable of being dried to form particles.

The particle forming step may be suitably used by a particle forming section and may further include a step of collecting the resultant particles (particle collecting step).

A method for drying of the liquid is selected depending on properties of the liquid. However, the method for drying of the liquid is not basically particularly limited and may be appropriately selected depending on the intended purpose, as long as the liquid is capable of being turned into a solid state. For example, when the liquid is a liquid in which solid raw materials are dissolved or dispersed in a volatile solvent, liquid droplets may be jetted and then dried in a conveying gas stream to volatilize the solvent. The solvent is capable of being dried to an arbitrary extent by appropriately selecting, for example, a temperature, a vapor pressure, and a kind of the gas to be jetted. It is not necessary to completely dry the liquid, as long as collected particles are kept in a solid state. The collected particles may be further dried in an additional step after collection. Alternatively, the liquid may be dried by utilizing, for example, a change in temperature or a chemical reaction.

<<Particle Collecting Step>>

The particle collecting step is a step of collecting dried particles.

The particle collecting step is capable of being suitably performed by a particle collecting section.

A volume average particle diameter (Dv) of the particles is not particularly limited and may be appropriately selected depending on the intended purpose, but is preferably 1 micrometer or more but 10 micrometers or less, more preferably 1 micrometer or more but 5 micrometers or less. When the volume average particle diameter (Dv) is 1 micrometer or more but 10 micrometers or less, a surface area per unit weight of each of the particles is capable of being kept large. As a result, advantageously, a dissolution amount per unit time of a drug is capable of being increased. When the volume average particle diameter (Dv) is less than 1 micrometer, the particles aggregate to each other. As a result, the particles are difficult to exist as primary particles.

A number average particle diameter (Dn) of the particles is not particularly limited and may be appropriately selected depending on the intended purpose, but is preferably 1 micrometer or more but 10 micrometers or less, more preferably 1 micrometer or more but 5 micrometers or less. When the volume average particle diameter (Dv) is 1 micrometer or more but 10 micrometers or less, a surface area per unit weight of each of the particles is capable of being kept large. As a result, advantageously, a dissolution amount per unit time of a drug is capable of being increased. When the volume average particle diameter (Dv) is less than 1 micrometer, the particles aggregate to each other. As a result, the particles are difficult to exist as primary particles.

A particle size distribution (volume average particle diameter/number average particle diameter) of the particles is not particularly limited and may be appropriately selected depending on the intended purpose, but is preferably 1.00 or more but 1.50 or less, more preferably 1.00 or more but 1.20 or less, particularly preferably 1.00 or more but 1.10 or less. When the particle size distribution (volume average particle diameter/number average particle diameter) is 1.00 or more but 1.50 or less, bioavailability of pharmaceuticals is capable of being improved due to narrowness of the particle size distribution. Note that, the volume average particle diameter, the number average particle diameter, and the particle size distribution are capable of being analyzed using, for example, a laser diffraction/scattering particle size distribution measurement device (device name: MICROTRAC MT 3000 II, available from MicrotracBEL Corp.).

The particle collecting section is not particularly limited and may be appropriately selected depending on the intended purpose. Examples of the particle collecting section include a cyclon collection and a back filter.

FIG. 9 is a schematic view illustrating one exemplary particle producing apparatus. A particle producing apparatus 1 mainly includes a liquid-droplet discharging section 2, a drying and collecting unit 60, a conveying-gas-stream outlet-port 65, and a particle storing section 63. The liquid-droplet discharging section 2 is coupled to a raw material container 13 and a liquid circulating pump 15, and is configured to supply the liquid 14 to the liquid-droplet discharging section 2 at any time. The raw material container 13 is configured to store the liquid 14. The liquid circulating pump 15 is configured to supply the liquid 14 stored in the raw material container 13 into the liquid-droplet discharging section 2 through a liquid supplying pipe 16 and to apply pressure to the liquid 14 in the liquid supplying pipe 16 to return the liquid to the raw material container 13 through a liquid returning pipe 22. The liquid supplying pipe 16 includes a pressure gauge P1, and the drying and collecting unit includes a pressure gauge P2. Pressure at which the liquid is fed into the liquid-droplet discharging section 2 and pressure inside a drying and collecting unit are managed by the pressure gauges P1, and P2. When a pressure value measured at the P1 is higher than a pressure value measured at the P2, the liquid 14 may disadvantageously leak out from discharging ports. When the pressure value measured at the P1 is lower than the pressure value measured at the P2, a gas may disadvantageously enter the liquid-droplet discharging section 2 to stop the liquid droplets from being discharged. Therefore, the pressure value measured at the P1 is preferably substantially the same as the pressure value measured at the P2.

A descending gas stream (conveying gas stream) 101 from a conveying-gas-stream inlet-port 64 is formed within a chamber 61. The liquid droplets 21 discharged from the liquid-droplet discharging section 2 are conveyed downward not only by gravity but also by the conveying gas stream 101, passed through a conveying-gas-stream outlet-port 65, collected by a particle collecting section 62, and stored in a toner storing section 63.

When jetted liquid droplets are brought into contact with each other prior to drying, the jetted liquid droplets are aggregated into one particle (hereinafter, this phenomenon may be referred to as coalescence). In order to obtain particles having a uniform particle diameter distribution, it is necessary to keep the jetted liquid droplets apart from each other. However, the liquid droplets are jetted at a certain initial velocity, but gradually slowed down due to air resistance. Therefore, the subsequent liquid droplets catch up with and coalesce with the preceding liquid droplets having been slowed down. This phenomenon occurs constantly. When the thus-coalesced particles are collected, the collected particles have a very poor particle diameter distribution. In order to prevent the liquid droplets from coalescing with each other, the liquid droplets are preferably dried and conveyed simultaneously, while preventing the liquid droplets from slowing down and from contacting with each other by the action of the conveying gas stream 101. Eventually, the particles are preferably conveyed to the particle collecting section.

For example, as illustrated in FIG. 9, when a portion of the conveying gas stream 101 is orientated in the same direction as a liquid-droplet discharging direction, as a first gas stream, adjacent to the liquid-droplet discharging section, the liquid droplets are capable of being prevented from slowing down immediately after the liquid droplets are discharged. As a result, the liquid droplets are capable of being prevented from coalescing with each other. FIG. 10 is a schematic view illustrating one exemplary gas stream path. The gas stream in the gas stream path 12 may be orientated in a direction transverse to the liquid-droplet discharging direction, as illustrated in FIG. 10. Alternatively, although not illustrated, the gas stream may be oriented at an angle, the angle being preferably determined so as to discharge the liquid droplets in a direction away from the liquid-droplet discharging section. When a coalescing preventing gas-stream is provided in the direction transverse to the liquid-droplet discharging direction as illustrated in FIG. 10, the coalescing preventing gas-stream is preferably orientated in a direction in which trajectories of the liquid droplets do not overlap with each other when the liquid droplets are conveyed from the discharging ports by the coalescing preventing gas-stream.

After coalescing is prevented by the first gas stream as described above, the dried particles may be conveyed to the particle collecting section by a second gas stream.

A velocity of the first gas stream is preferably equal to or higher than a velocity at which the liquid droplets are jetted. When a velocity of the coalescing preventing gas-stream is lower than the velocity at which the liquid droplets are jetted, the coalescing preventing gas-stream is difficult to exert a function of preventing the liquid droplets from contacting with each other, the function being the essential purpose of the coalescing preventing gas-stream.

The first gas stream may have an additional property so as to prevent the liquid droplets from coalescing with each other. The first gas stream may not necessarily have the same properties as the second gas stream. The coalescing preventing gas-stream may be added with a chemical substance or may be subjected to a promising physical treatment, the chemical substance or the physical treatment having a function to promote drying of surfaces of the particles.

The conveying gas stream 101 is not limited in terms of a state of gas stream. Examples of the state include laminar flow, swirl flow, and turbulent flow. A kind of a gas constituting the conveying gas stream 101 is not particularly limited and may be appropriately selected depending on the intended purpose. Examples of the kind include air and incombustible gases (e.g., nitrogen). A temperature of the conveying gas stream 101 may be adjusted appropriately, and is preferably constant during production. The chamber 61 may include a section configured to change the state of the conveying gas stream 101. The conveying gas stream 101 may be used not only for preventing the liquid droplets 21 from coalescing with each other but also for preventing the liquid droplets from depositing on the chamber 61.

When particles collected by the particle collecting section illustrated in FIG. 9 includes a large amount of a residual solvent, secondary drying is performed in order to reduce the residual solvent, if necessary. The secondary drying may be performed using commonly known drying sections such as fluid bed drying and vacuum drying. When the solvent remains in the particles, properties of the particles (e.g., heat resistant storability, fixability, and chargeability) are changed over time. Additionally, the solvent is volatilized during heat-fixing, which increases the possibility that users and peripheral devices are adversely affected. Therefore, the particles are preferably dried sufficiently.

<Administration Route>

An administration route of the pharmaceuticals is not particularly limited and may be appropriately selected depending on the intended purpose. Examples of the administration route include oral administration, nasal administration, rectal administration, vaginal administration, subcutaneous administration, intravenous administration, and pulmonary administration. Among them, oral administration is preferable.

EXAMPLES

Examples of the present invention will now be described, but the present invention is not limited to the Examples in any way.

Note that, a volume average particle diameter (Dv), a number average particle diameter (Dn), and a particle size distribution (Dv/Dn) of the resultant particles were measured using a laser diffraction/scattering particle size distribution measurement device (device name: MICROTRAC MT 3000 II, available from MicrotracBEL Corp.).

(Production Example of Particles by Liquid-Column Resonance Method)

Example 1

Cyclosporine (product name: CYCLOSPORIN A, available from Tokyo Chemical Industry Co., Ltd.) (0.5 parts by mass), hydroxypropylcellulose (HPC-SSL, weight average molecular weight: 15,000 or more but 30,000 or less, viscosity at 20 degrees Celsius: 2.0 mPa·s or more but 2.9 mPa·s or less, available from Nippon Soda Co., Ltd.) (9.5 parts by mass), and ethanol (available from KANTO CHEMICAL CO., INC.) (500 parts by mass) were mixed and stirred using a stirrer (device name: magnetic stirrer, available from AS ONE Corporation) at 1,000 rpm for 1 hour to obtain a mixed solution. The resultant mixed solution was filtered through a filter having an average pore diameter of 1 micrometer (product name: MILLEX, available from Merck) to obtain a Liquid A. A specific gravity of the Liquid A was 0.821.

The resultant Liquid A was discharged from discharging ports using a liquid-column resonance liquid-droplet discharging device (device name: GEN4, available from Ricoh Company, Ltd.) to form liquid droplets. The liquid-column resonance liquid-droplet discharging device was the device illustrated in FIG. 1, the device having been modified to have one discharging port per one liquid-column resonance liquid-chamber. The resultant liquid droplets were dried using the device illustrated in FIG. 9 to obtain pharmaceutical particles. The resultant pharmaceutical particles were found to have a volume average particle diameter (Dv) of 3.50 micrometers, a number average particle diameter (Dn) of 3.33 micrometers, and a particle size distribution (Dv/Dn) of 1.05. Note that, the below-described conditions were used. Composition and physical properties of the resultant pharmaceutical particles are described in Tables 1 to 2-2 below.

-Liquid-Column Resonance Condition-
Resonance mode: N=2
Length between both ends of liquid-column resonance liquid-chamber in longitudinal direction: L=1.8 mm
Height of frame end of liquid-column resonance liquid-chamber at common liquid supplying-path side: h1=80 micrometers
Height of communication port of liquid-column resonance liquid-chamber: h2=40 micrometers
-Particle Production Condition-
Shape of discharging port: perfect circle
Diameter of discharging port: 8.0 micrometers
Number of discharging port: 1 (per one liquid-column resonance liquid-chamber)
Number of liquid-column resonance liquid-chamber: 384
Temperature of dry air: 40 degrees Celsius
Flow rate of dry air: dry nitrogen in device of 100 L/min
Applied voltage: 12.0 V
Driving frequency: 310 kHz Example 2

Tranilast (product name: TRANILAST, available from Tokyo Chemical Industry Co., Ltd.) (0.5 parts by mass), hydroxypropylcellulose (HPC-SSL, weight average molecular weight: 15,000 or more but 30,000 or less, viscosity at 20 degrees Celsius: 2.0 mPa·s or more but 2.9 mPa·s or less, available from Nippon Soda Co., Ltd.) (9.5 parts by mass), and 1,4-dioxane (available from Hayashi Pure Chemical Ind., Ltd.) (500 parts by mass) were mixed and stirred using a stirrer (device name: magnetic stirrer, available from AS ONE Corporation) at 1,000 rpm for 1 hour to obtain a mixed solution. The resultant mixed solution was filtered through a filter having an average pore diameter of 1 micrometer (product name: MILLEX, available from Merck) to obtain a Liquid B. A specific gravity of the Liquid B was 1.1888.

Pharmaceutical particles were obtained in the same manner as in Example 1, except that the Liquid A was changed to the Liquid B. Composition and physical properties of the resultant pharmaceutical particles are described in Tables 1 to 2-2 below.

Example 3

Calcitonin (product name: CALCITONIN SALMON "ITO," available from ILS Inc.) (0.3 parts by mass), lactic acid-glycolic acid copolymer (PLGA, product name: PLGA 7510, available from Wako Pure Chemical Industries, Ltd.) (29.7 parts by mass), and acetone (available from KOKUSAN CHEMICAL Co., Ltd.) (970 parts by mass) were mixed and stirred using a stirrer (device name: magnetic stirrer, available from AS ONE Corporation) at 1,000 rpm for 1 hour to obtain a mixed solution. The resultant mixed solution was filtered through a filter having an average pore diameter of 1 micrometer (product name: MILLEX, available from Merck) to obtain a Liquid C. A specific gravity of the Liquid C was 0.805.

Pharmaceutical particles were obtained in the same manner as in Example 1, except that the Liquid A was changed to the Liquid C and the temperature of dry air in the particle production condition was changed to 65 degrees Celsius. Composition and physical properties of the resultant pharmaceutical particles are described in Tables 1 to 2-2 below.

Example 4

Quercetin (product name: QUERCETIN, available from Tokyo Chemical Industry Co., Ltd.) (3 parts by mass), SOLUPLUS (available from BASF) (27 parts by mass), and ethanol (available from KANTO CHEMICAL CO., INC.) (970 parts by mass) were mixed and stirred using a stirrer (device name: magnetic stirrer, available from AS ONE Corporation) at 1,000 rpm for 1 hour to obtain a mixed solution. The resultant mixed solution was filtered through a filter having an average pore diameter of 1 micrometer (product name: MILLEX, available from Merck) to obtain a Liquid D. A specific gravity of the Liquid D was 0.798.

Pharmaceutical particles were obtained in the same manner as in Example 1, except that the Liquid A was changed to the Liquid D and the temperature of dry air in the particle production condition was changed to 50 degrees Celsius. Composition and physical properties of the resultant pharmaceutical particles are described in Tables 1 to 2-2 below.

Example 5

Metformin (product name: METFORMIN HYDROCHLORIDE, available from Tokyo Chemical Industry Co., Ltd.) (20 parts by mass), EUDRAGIT RSPO (available from Evonik Industries) (27 parts by mass), EUDRAGIT RLPO (available from Evonik Industries) (3 parts by mass), ethanol (available from KANTO CHEMICAL CO., INC.) (828 parts by mass), and ion-exchanged water (122 parts by mass) were mixed and stirred using a stirrer (device name: magnetic stirrer, available from AS ONE Corporation) at 1,000 rpm for 1 hour to obtain a mixed solution. The resultant mixed solution was filtered through a filter having an average pore diameter of 1 micrometer (product name: MILLEX, available from Merck) to obtain a Liquid E. A specific gravity of the Liquid E was 0.840.

Pharmaceutical particles were obtained in the same manner as in Example 1, except that the Liquid A was changed to the Liquid E and the temperature of dry air in the particle production condition was changed to 50 degrees Celsius. Composition and physical properties of the resultant pharmaceutical particles are described in Tables 1 to 2-2 below.

Example 6

Metformin (product name: METFORMIN HYDROCHLORIDE, available from Tokyo Chemical Industry Co., Ltd.) (25 parts by mass), EUDRAGIT RSPO (available from Evonik Industries) (22.5 parts by mass), EUDRAGIT RLPO (available from Evonik Industries) (2.5 parts by mass), ethanol (available from KANTO CHEMICAL CO., INC.) (828 parts by mass), and ion-exchanged water (122 parts by mass) were mixed and stirred using a stirrer (device name: magnetic stirrer, available from AS ONE Corporation) at 1,000 rpm for 1 hour to obtain a mixed solution. The resultant mixed solution was filtered through a filter having an average pore diameter of 1 micrometer (product name: MILLEX, available from Merck) to obtain a Liquid F. A specific gravity of the Liquid F was 0.841.

Pharmaceutical particles were obtained in the same manner as in Example 1, except that the Liquid A was changed to the Liquid F and the temperature of dry air in the particle production condition was changed to 50 degrees Celsius. Composition and physical properties of the resultant pharmaceutical particles are described in Tables 1 to 2-2 below.

Example 7

Metformin (product name: METFORMIN HYDROCHLORIDE, available from Tokyo Chemical Industry Co., Ltd.) (30 parts by mass), EUDRAGIT RSPO (available from Evonik Industries) (18 parts by mass), EUDRAGIT RLPO (available from Evonik Industries) (2 parts by mass), ethanol (available from KANTO CHEMICAL CO., INC.) (828 parts by mass), and ion-exchanged water (122 parts by mass) were mixed and stirred using a stirrer (device name: magnetic stirrer, available from AS ONE Corporation) at 1,000 rpm for 1 hour to obtain a mixed solution. The resultant mixed solution was filtered through a filter having an average pore diameter of 1 micrometer (product name: MILLEX, available from Merck) to obtain a Liquid G. A specific gravity of the Liquid G was 0.843.

Pharmaceutical particles were obtained in the same manner as in Example 1, except that the Liquid A was changed to the Liquid G and the temperature of dry air in the particle production condition was changed to 50 degrees Celsius. Composition and physical properties of the resultant pharmaceutical particles are described in Tables 1 to 2-2 below.

Example 8

Allopurinol (product name: ALLOPURINOL, available from Tokyo Chemical Industry Co., Ltd.) (0.75 parts by mass), HPMCAs-HG (available from Shin-Etsu Chemical Co., Ltd.) (14.25 parts by mass), methanol (available from Wako Pure Chemical Industries, Ltd.) (788 parts by mass), and acetone (available from KOKUSAN CHEMICAL Co., Ltd.) (197 parts by mass) were mixed and stirred using a stirrer (device name: magnetic stirrer, available from AS ONE Corporation) at 1,000 rpm with heating at 50 degrees Celsius by a heating device (device name: TBS201RA, available from ADVANTEC) for 1 hour to obtain a mixed solution. The resultant mixed solution was filtered through a filter having an average pore diameter of 1 micrometer (product name: MILLEX, available from Merck) to obtain a Liquid H. A specific gravity of the Liquid H was 0.803.

Pharmaceutical particles were obtained in the same manner as in Example 1, except that the Liquid A was changed to the Liquid H and the temperature of dry air in the particle production condition was changed to 50 degrees Celsius. Composition and physical properties of the resultant pharmaceutical particles are described in Tables 1 to 2-2 below.

Example 9

Prednisolone (product name: Prednisolone, available from Tokyo Chemical Industry Co., Ltd.) (0.15 parts by mass), guar gum (product name: RG-100, available from Mitsubishi-Kagaku Foods Corporation) (0.85 parts by mass), ion-exchanged water (799 parts by mass), and ethanol (available from KANTO CHEMICAL CO., INC.) (200 parts by mass) were mixed and stirred using a stirrer (device name: magnetic stirrer, available from AS ONE Corporation) at 1,000 rpm for 1 hour to obtain a mixed solution. The resultant mixed solution was filtered through a filter having an average pore diameter of 1 micrometer (product name: MILLEX, available from Merck) to obtain a Liquid I. A specific gravity of the Liquid I was 0.959.

Pharmaceutical particles were obtained in the same manner as in Example 1, except that the Liquid A was changed to the Liquid I and the temperature of dry air in the particle production condition was changed to 150 degrees Celsius. Composition and physical properties of the resultant pharmaceutical particles are described in Tables 1 to 2-2 below.

(Production example of particles by membrane-vibration method)

Comparative Example 1

The Liquid A was obtained in the same manner as in Example 1.

The resultant Liquid A was discharged from discharging ports of a nozzle plate using a membrane-vibration particle producing device (membrane-vibration nozzle of DEODORANT PUFF PUFF, available from JOHNSON COMPANY, LIMITED) to form liquid droplets. The resultant liquid droplets were dried to obtain pharmaceutical particles. Note that, the below-described conditions were used. Composition and physical properties of the resultant pharmaceutical particles are described in Tables 1 to 2-2 below.

-Membrane-Vibration Condition-
Outer diameter of nozzle plate: 8.0 mm
Average thickness of nozzle plate: 20 micrometers
Material of nozzle plate: Nickel plate
-Particle Production Condition-
Shape of discharging port: perfect circle
Diameter of discharging port: 5 micrometers
Number of discharging port: 85
Temperature of dry air: 27 degrees Celsius or more but 28 degrees Celsius or less
Flow rate of dry air: dry nitrogen in device of 30.0 L/min
Dew point temperature: −20.0 degrees Celsius
Applied voltage: 20.0 V
Driving frequency: 52 kHz Comparative Example 2

The Liquid B was obtained in the same manner as in Example 2.

Pharmaceutical particles were obtained in the same manner as in Comparative Example 1, except that the Liquid A was changed to the Liquid B. Composition and physical properties of the resultant pharmaceutical particles are described in Tables 1 to 2-2 below.

Comparative Example 3

The Liquid C was obtained in the same manner as in Example 3.

Pharmaceutical particles were obtained in the same manner as in Comparative Example 1, except that the Liquid A was changed to the Liquid C and the temperature of dry air in the particle production condition was changed to 65 degrees Celsius or more but 66 degrees Celsius or less. Composition and physical properties of the resultant pharmaceutical particles are described in Tables 1 to 2-2 below.

Comparative Example 4

The Liquid D was obtained in the same manner as in Example 4.

Pharmaceutical particles were obtained in the same manner as in Comparative Example 1, except that the Liquid A was changed to the Liquid D and the temperature of dry air in the particle production condition was changed to 50 degrees Celsius or more but 51 degrees Celsius or less. Composition and physical properties of the resultant pharmaceutical particles are described in Tables 1 to 2-2 below.

(Production example of particles by liquid-vibration method)

Comparative Example 5

The Liquid A was obtained in the same manner as in Example 1.

The resultant Liquid A was discharged from discharging ports using a liquid-vibration particle producing device (device described in Example 1 of Japanese Patent No. 5315920) to form liquid droplets. The resultant liquid droplets were dried to obtain pharmaceutical particles. Note that, the below-described conditions were used. Composition and physical properties of the resultant pharmaceutical particles are described in Tables 1 to 2-2 below.

-Particle Production Condition-
Shape of discharging port: perfect circle
Diameter of discharging port: 8 micrometers
Number of discharging port: 300
Temperature of dry air: 27 degrees Celsius or more but 28 degrees Celsius or less
Flow rate of dry air: dry nitrogen in device of 30.0 L/min
Applied voltage: 20.0 V
Driving frequency: 30 kHz Comparative Example 6

The Liquid B was obtained in the same manner as in Example 2.
Pharmaceutical particles were obtained in the same manner as in Comparative Example 5, except that the Liquid A was changed to the Liquid B. Composition and physical properties of the resultant pharmaceutical particles are described in Tables 1 to 2-2 below.

Comparative Example 7

The Liquid F was obtained in the same manner as in Example 6.
Pharmaceutical particles were obtained in the same manner as in Comparative Example 5, except that the Liquid A was changed to the Liquid F and the temperature of dry air in the particle production condition was changed to 50 degrees Celsius or more but 51 degrees Celsius or less. Composition and physical properties of the resultant pharmaceutical particles are described in Tables 1 to 2-2 below.

(Production Example of Particles by Spray-Drying Method)

Comparative Example 8

The Liquid A was obtained in the same manner as in Example 1.
The resultant Liquid A was discharged using a spray-drying particle producing device (device: 6552-1/8 JAC miniature type, available from SPRAYING SYSTEMS CO., JAPAN) to form liquid droplets. The resultant liquid droplets were dried to obtain pharmaceutical particles. Note that, the below-described conditions were used. Composition and physical properties of the resultant pharmaceutical particles are described in Tables 1 to 2-2 below.

-Particle Production Condition-
Diameter of nozzle: 0.5 mm
Air pressure: 0.1 MPa
Temperature of dry air: 40 degrees Celsius Comparative Example 9

The Liquid B was obtained in the same manner as in Example 2.
Pharmaceutical particles were obtained in the same manner as in Comparative Example 8, except that the Liquid A was changed to the Liquid B and the temperature of dry air in the particle production condition was changed to 50 degrees Celsius. Composition and physical properties of the resultant pharmaceutical particles are described in Tables 1 to 2-2 below.

Comparative Example 10

The Liquid H was obtained in the same manner as in Example 8.
Pharmaceutical particles were obtained in the same manner as in Comparative Example 8, except that the Liquid A was changed to the Liquid H and the temperature of dry air in the particle production condition was changed to 150 degrees Celsius. Composition and physical properties of the resultant pharmaceutical particles are described in Tables 1 to 2-2 below.

Comparative Example 11

The Liquid I was obtained in the same manner as in Example 9.
Pharmaceutical particles were obtained in the same manner as in Comparative Example 8, except that the Liquid A was changed to the Liquid I. Composition and physical properties of the resultant pharmaceutical particles are described in Tables 1 to 2-2 below.

The methods of Examples 1 to 9 and Comparative Examples 1 to 11 were used to evaluate "particle size distribution (Dv/Dn)" and "continuous productivity" as described below.

(Particle Size Distribution (Dv/Dn))

The pharmaceutical particles of Examples 1 to 9 and Comparative Examples 1 to 11 were measured for the particle size distribution (Dv/Dn) using a laser diffraction/scattering particle size distribution measurement device (device name: MICROTRAC MT 3000 II, available from MicrotracBEL Corp.). The "particle size distribution (Dv/Dn)" was evaluated based on the below-described evaluation criteria.

-Evaluation Criteria-
A: 1.00 or more but 1.20 or less
B: More than 1.20 but 1.50 or less
C: More than 1.50

(Continuous Productivity)

The methods of Examples 1 to 9 and Comparative Examples 1 to 11 were measured for a weight of particles jetted from 0 through 60 seconds after initiation of discharging (early stage) (jetted weight at early stage) and a weight of particles jetted from 540 through 600 seconds after initiation of discharging (end stage) (jetted weight at end stage) using a gravimeter (device name: GX-3000, available from A&D Company, Limited). The jetted weight at early stage and the jetted weight at end stage were used to calculate a decreasing rate of yield according to Expression A below. The "continuous productivity" was evaluated based on evaluation criteria described below.

Decreasing rate of yield(%)=[(Jetted weight at early stage−Jetted weight at end stage)/Jetted weight at early stage]×100      Expression A -Evaluation Criteria-
A: The decreasing rate is less than 5%.
B: The decreasing rate is 5% or more but less than 25%.
C: The decreasing rate is 25% or more.

TABLE 1

|  | | Liquid name | Physiologically active substance | Disparsing agent | Solvent |
|---|---|---|---|---|---|
| Example | 1 | Liquid A | Cyclosporine | HPC-SSL | Ethanol |
|  | 2 | Liquid B | Tranilast | HPC-SSL | 1,4-Dioxane |
|  | 3 | Liquid C | Calcitonin | PLGA | Acetone |
|  | 4 | Liquid D | Quercetin | SOLUPLUS | Ethanol |
|  | 5 | Liquid E | Metformin | EUDRAGIT RSPO/ EUDRAGIT RLPO | Ethanol/Water |
|  | 6 | Liquid F | Metformin | EUDRAGIT RSPO/ EUDRAGIT RLPO | Ethanol/Water |
|  | 7 | Liquid G | Metformin | EUDRAGIT RSPO/ EUDRAGIT RLPO | Ethanol/Water |
|  | 8 | Liquid H | Allopurinol | HPMCAs-HG | Methanol/Acetone |
|  | 9 | Liquid I | Prednisolone | Guar gum | Ethanol/Water |
| Comparative Example | 1 | Liquid A | Cyclosporine | HPC-SSL | Ethanol |
|  | 2 | Liquid B | Tranilast | HPC-SSL | 1,4-Dioxane |
|  | 3 | Liquid C | Calcitonin | PLGA | Acetone |
|  | 4 | Liquid D | Quercetin | SOLUPLUS | Ethanol |
|  | 5 | Liquid A | Cyclosporine | HPC-SSL | Ethanol |
|  | 6 | Liquid B | Tranilast | HPC-SSL | 1,4-Dioxane |
|  | 7 | Liquid F | Metformin | EUDRAGIT RSPO/ EUDRAGIT RLPO | Ethanol/Water |
|  | 8 | Liquid A | Cyclosporine | HPC-SSL | Ethanol |
|  | 9 | Liquid B | Tranilast | HPC-SSL | 1,4-Dioxane |
|  | 10 | Liquid H | Allopurinol | HPMCAs-HG | Methanol/Acetone |
|  | 11 | Liquid I | Prednisolone | Guar gum | Ethanol/Water |

Note that, product names and manufacturer names of the components described in Table 1 are as follows.

Cyclosporine: available from Tokyo Chemical Industry Co., Ltd., product name: CYCLOSPORIN A.
Tranilast: available from Tokyo Chemical Industry Co., Ltd., product name: TRANILAST
Calcitonin: available from ILS Inc., product name: CALCITONIN SALMON "ITO"
Quercetin: available from Tokyo Chemical Industry Co., Ltd., product name: QUERCETIN
Metformin: available from Tokyo Chemical Industry Co., Ltd., product name: METFORMIN HYDROCHLORIDE
Allopurinol: available from Tokyo Chemical Industry Co., Ltd., product name: ALLOPURINOL
Prednisolone: available from Tokyo Chemical Industry Co., Ltd., product name: PREDNISOLONE
HPC-SSL: hydroxypropylcellulose, available from Nippon Soda Co., Ltd., weight average molecular weight: 15,000 or more but 30,000 or less, viscosity at 20 degrees Celsius: 2.0 mPa·s or more but 2.9 mPa·s or less
PLGA: available from Wako Pure Chemical Industries, Ltd., product name: PLGA7510
SOLUPLUS: available from BASF
EUDRAGIT RSPO: available from Evonik Industries
EUDRAGIT RLPO: available from Evonik Industries
HPMCAs-HG: available from Shin-Etsu Chemical Co., Ltd.
Guar gum: available from Mitsubishi-Kagaku Foods Corporation, Product name: RG-100
Ethanol: available from KANTO CHEMICAL CO., INC.
1,4-Dioxane: available from Hayashi Pure Chemical Ind., Ltd.
Acetone: available from KOKUSAN CHEMICAL Co., Ltd.
Methanol: available from Wako Pure Chemical Industries, Ltd.

TABLE 2-1

| | | Discharging method | Frequency (kHz) | Volume average particle diameter (Dv) (μm) | Number average particle diameter (Dn) (μm) | Particle size distribution (Dv/Dn) | Decreasing rate of yield (%) |
|---|---|---|---|---|---|---|---|
| Example | 1 | Liquid-column resonance method | 310 | 3.5 | 3.33 | 1.05 | 2.1 |
|  | 2 | Liquid-column resonance method | 310 | 3.5 | 3.33 | 1.05 | 1.9 |
|  | 3 | Liquid-column resonance method | 310 | 3.84 | 3.5 | 1.1 | 1.1 |
|  | 4 | Liquid-column resonance method | 310 | 4.6 | 4 | 1.15 | 4.5 |
|  | 5 | Liquid-column resonance method | 310 | 5.25 | 4.75 | 1.11 | 2.3 |
|  | 6 | Liquid-column resonance method | 150 | 5.77 | 5.3 | 1.09 | 2.6 |
|  | 7 | Liquid-column resonance method | 310 | 5.45 | 5.21 | 1.05 | 2.5 |
|  | 8 | Liquid-column resonance method | 310 | 4.62 | 4.35 | 1.06 | 2.6 |
|  | 9 | Liquid-column resonance method | 310 | 1.3 | 1.11 | 1.17 | 4.9 |

TABLE 2-1-continued

| | | Discharging method | Frequency (kHz) | Volume average particle diameter (Dv) (μm) | Number average particle diameter (Dn) (μm) | Particle size distribution (Dv/Dn) | Decreasing rate of yield (%) |
|---|---|---|---|---|---|---|---|
| Comparative Example | 1 | Membrane-vibration method | 52 | 3.6 | 3.43 | 1.05 | 45.3 |
| | 2 | Membrane-vibration method | 52 | 3.5 | 3.37 | 1.04 | 44.6 |
| | 3 | Membrane-vibration method | 52 | 3.92 | 3.65 | 1.07 | 32.9 |
| | 4 | Membrane-vibration method | 52 | 3.95 | 3.78 | 1.04 | 69.2 |
| | 5 | Liquid-vibration method | 30 | 3.6 | 3.43 | 1.05 | 38 |
| | 6 | Liquid-vibration method | 30 | 3.5 | 3.37 | 1.04 | 40.8 |
| | 7 | Liquid-vibration method | 30 | 4.87 | 4.62 | 1.05 | 37.7 |
| | 8 | Spray-drying method | — | 5.99 | 3.24 | 1.85 | 5.3 |
| | 9 | Spray-drying method | — | 5.86 | 3.15 | 1.86 | 4.5 |
| | 10 | Spray-drying method | — | 4.86 | 2.14 | 2.27 | 4.4 |
| | 11 | Spray-drying method | — | 8.43 | 1.17 | 7.21 | 7.9 |

TABLE 2-2

| | | Evaluation result | | |
|---|---|---|---|---|
| | | Particle size distribution | Continuous productivity | Comprehensive evaluation |
| Example | 1 | A | A | A |
| | 2 | A | A | A |
| | 3 | A | A | A |
| | 4 | A | A | A |
| | 5 | A | A | A |
| | 6 | A | A | A |
| | 7 | A | A | A |
| | 8 | A | A | A |
| | 9 | A | A | A |
| Comparative Example | 1 | A | C | C |
| | 2 | A | C | C |
| | 3 | A | C | C |
| | 4 | A | C | C |
| | 5 | A | C | C |
| | 6 | A | C | C |
| | 7 | A | C | C |
| | 8 | C | B | C |
| | 9 | C | A | C |
| | 10 | C | A | C |
| | 11 | C | B | C |

Test Example 1

The pharmaceutical particles produced in Example 1 were used to perform an evaluation test for dissolution property.

The pharmaceutical particles (60 mg) was added to ion-exchanged water (100 mg) and stirred at 50 rpm at 37 degrees Celsius for 60 minutes. Then, the "dissolution property" was evaluated. The results are presented in Table 3 and FIG. 11.

Test Example 2

The "dissolution property" was evaluated in the same manner as in Test Example 1, except that the pharmaceutical particles produced in Example 1 were changed to cyclosporine bulk powder (product name: CYCLOSPORIN A, available from Tokyo Chemical Industry Co., Ltd.). The results are presented in Table 3 and FIG. 11.

TABLE 3

| | | Dissolution amount (μg/mL) | |
|---|---|---|---|
| | | Test Example 1 | Test Example 2 |
| Time (min) | 0 | 0 | 0 |
| | 3 | 1.02 ± 0.09 | 0.01 ± 0.01 |
| | 5 | 1.70 ± 0.33 | 0.00 ± 0.00 |
| | 7 | 1.79 ± 0.37 | 0.08 ± 0.05 |
| | 10 | 2.24 ± 0.46 | 0.01 ± 0.01 |
| | 20 | 4.64 ± 0.70 | 0.10 ± 0.06 |
| | 40 | 7.53 ± 0.77 | 0.04 ± 0.02 |
| | 60 | 11.75 ± 0.81 | 0.01 ± 0.01 |

Note that, the values of dissolution amount (n=3) in Table 3 are expressed as average±standard error.

It was seen from the result of Table 3 and FIG. 11 that the pharmaceutical particles of Example 1 improved the dissolution rate and the dissolution amount of cyclosporine and exhibited sustained release dissolution. It is presumed that the pharmaceutical particles are gradually dissolved because high-density particles are formed and then formed into a polymer matrix with HPC-SSL through production of the pharmaceuticals by the liquid-column resonance method.

Test Example 3

The pharmaceutical particles produced in Example 2 were used to perform an evaluation test for dissolution property.

The pharmaceutical particles (63 mg) was added to a dissolution liquid (pH 1.2) (liquid made by adding 7.0 mL of hydrochloric acid to 2.0 g of sodium chloride and adding water to 1,000 mL) (900 mL) and stirred at 50 rpm at 37 degrees Celsius for 120 minutes. Then, the "dissolution property" was evaluated. The results are presented in Table 4 and FIG. 12.

Test Example 4

The "dissolution property" was evaluated in the same manner as in Test Example 3, except that the pharmaceutical particles produced in Example 2 were changed to tranilast bulk powder (product name: TRANILAST, available from Tokyo Chemical Industry Co., Ltd.). The results are presented in Table 4 and FIG. 12.

TABLE 4

|  |  | Dissolution amount (μg/mL) | |
|---|---|---|---|
|  |  | Test Example 3 | Test Example 4 |
| Time (min) | 0 | 0 | 0 |
|  | 5 | 0.75 ± 0.08 | 0.00 ± 0.00 |
|  | 10 | 0.77 ± 0.03 | 0.00 ± 0.00 |
|  | 20 | 0.97 ± 0.11 | 0.00 ± 0.00 |
|  | 40 | 1.06 ± 0.07 | 0.00 ± 0.00 |
|  | 60 | 1.21 ± 0.03 | 0.00 ± 0.00 |
|  | 120 | 1.47 ± 0.03 | 0.03 ± 0.00 |

Note that, the values of dissolution amount (n=3) in Table 4 are expressed as average±standard error.

It was seen from the result of Table 4 and FIG. 12 that the pharmaceutical particles of Example 2 exhibited an immediate release property and improved the dissolution rate and the dissolution amount of tranilast. It is presumed that the tranilast was formed into a solid dispersion in which the tranilast is uniformly dispersed in HPC serving as a dispersing agent through production of the pharmaceuticals by the liquid-column resonance method. As a result, the pharmaceutical compound included in the solid dispersion was improved in wetting property and decreased in particle diameter, leading to improved dissolution property.

Test Example 5

In order to evaluate an oral absorbability of the pharmaceutical particles produced in Example 1, the pharmaceutical particles of Example 1 and CYCLOSPORIN A bulk powder were orally administrated to male SD rats (from 6 to 8 week-old, available from Japan SLC, Inc.) and then blood drug concentrations were measured over time. Each powder was suspended in water and administrated through a single-dose forced oral administration to the male SD rats at 10 mg/kg in terms of CYCLOSPORIN A. After the oral administration, blood was collected from tail veins over time, transferred to heparinized micro test tubes, and cooled with ice immediately. After the cooling, the blood was rapidly centrifuged to obtain blood plasma. The resultant blood plasma was quantified by an ultra-high performance liquid chromatography (available from Waters) equipped with, as a detector, a single quadrupole mass spectrometer (device name: ACQUITY SQD, available from Waters). The results are presented in FIG. 13. Pharmacokinetic parameters calculated from the results of blood drug concentrations are presented in Table 5 below. Note that, $C_{max}$ denotes a maximum blood concentration (concentration at a peak in a blood concentration curve), $T_{max}$ denotes time to reach the maximum blood concentration (time to reach the peak in the blood concentration curve), $T_{1/2}$ denotes a half-life of the blood drug concentration, and $AUC_{0-\infty}$ denotes an area under the blood concentration curve from initiation of administration to drug elimination.

TABLE 5

|  | $C_{max}$ (mg/mL) | $T_{max}$ (h) | $T_{1/2}$ (h) | $AUC_{0-\infty}$ (mg · h/mL) | Bioavailability (%) |
|---|---|---|---|---|---|
| CYCLOSPORIN A bulk powder | 0.1 ± 0.1 | 3.4 ± 0.4 | 2.4 ± 0.2 | 0.6 ± 0.3 | 0.7 |
| Pharmaceutical particles of Example 1 | 1.1 ± 0.1 | 3.8 ± 1.0 | 4.7 ± 1.0 | 11.4 ± 2.3 | 12.3 |

Note that, the pharmacokinetic parameters in Table 5 are expressed as average±standard error (n=5).

For the results of Table 5 and FIG. 13, the pharmaceutical particles prepared in Example 1 drastically improved the oral absorbability of the CYCLOSPORIN A, where the $C_{max}$ and the $AUC_{0-\infty}$ were significantly higher (i.e., 11-fold and 19-fold, respectively) (Fisher's least significant difference test, p<0.05). That is, the bioavailability was significantly improved. The $T_{1/2}$ was 2.3 hours longer than $T_{1/2}$ of the CYCLOSPORIN A bulk powder. The pharmaceutical particles of Example 1 exhibited increased retentivity in blood of CYCLOSPORIN A. It is presumed that this is because the pharmaceutical particles prepared in Example 1 have a sustained release drug dissolution property.

Test Example 6

In order to evaluate an oral absorbability of the pharmaceutical particles produced in Example 2, the pharmaceutical particles of Example 2 and TRANILAST bulk powder were orally administrated to male SD rats (from 6 to 8 week-old, available from Japan SLC, Inc.) and then blood drug concentrations were measured over time. Each powder was suspended in water and administrated through a single-dose forced oral administration to the male SD rats at 10 mg/kg in terms of TRANILAST. After the oral administration, blood was collected from tail veins over time, transferred to heparinized micro test tubes, and cooled with ice immediately. After the cooling, the blood was rapidly centrifuged to obtain blood plasma. The resultant blood plasma was quantified by an ultra-high performance liquid chromatography (available from Waters) equipped with, as a detector, a single quadrupole mass spectrometer (ACQUITY SQD, available from Waters). The results are presented in FIG. 14. Pharmacokinetic parameters calculated from the results of blood drug concentrations are presented in Table 6 below.

TABLE 6

|  | $C_{max}$ (mg/mL) | $T_{max}$ (h) | $T_{1/2}$ (h) | $AUC_{0-\infty}$ (mg · h/mL) | Bioavailability (%) |
|---|---|---|---|---|---|
| TRANILAST bulk powder | 0.1 ± 0.0 | 1.8 ± 0.7 | 2.9 ± 0.7 | 0.8 ± 0.4 | 1.2 |
| Pharmaceutical particles of Example 2 | 11.2 ± 2.0 | 0.3 ± 0.0 | 0.4 ± 0.0 | 12.7 ± 0.6 | 19 |

Note that, the pharmacokinetic parameters in Table 6 are expressed as average±standard error (n=4).

For the results of Table 6 and FIG. 14, the pharmaceutical particles prepared in Example 2 drastically improved the oral absorbability of the TRANILAST, where the $C_{max}$ and the $AUC_{0-\infty}$ were significantly higher (i.e., 112-fold and 16-fold, respectively)

(Fisher's least significant difference test, p<0.05). That is, the bioavailability was significantly improved. The $T_{max}$ of the pharmaceutical particles prepared in Example 2 was 1.5 hours shorter than $T_{max}$ of the TRANILAST bulk powder. Therefore, a drug absorption rate was confirmed to be improved. It is presumed that this is because the pharmaceutical particles prepared in Example 2 have an instant drug dissolution property.

Test Example 7

The pharmaceutical particles produced in Example 3 were used to perform an evaluation test for dissolution property.

Ten milligrams of the pharmaceutical particles were added to 100 mL of an intrapulmonary-environment imitating liquid (0.169 g of magnesium chloride, 5.016 g of sodium chloride, 0.249 g of potassium chloride, 0.059 g of anhydrous sodium sulfate, 0.306 g of calcium chloride dehydrate, 0.794 g of sodium acetate trihydrate, 2.170 g of sodium hydrogen carbonate, 0.080 g of sodium citrate dehydrate, 0.118 g of disodium hydrogen-phosphate, and 0.167 g of dipalmitoylphosphatidylcholine in 1 L of water). The resultant was shaken at a shaking rate of 30 spm at 37 degrees Celsius for 24 hours. Thus, the "dissolution property" was evaluated. The results are presented in Table 7 below and FIG. 15.

TABLE 7

| | | Dissolution amount (μg/mL) | |
|---|---|---|---|
| | | Calcitonin bulk powder | Pharmaceutical particles of Example 3 |
| Time (hour) | 0 | 0 | 0 |
| | 0.25 | 9.56 ± 0.03 | 0.94 ± 0.24 |
| | 0.5 | 9.88 ± 0.13 | 0.80 ± 0.58 |
| | 1 | 9.68 ± 0.20 | 1.80 ± 0.21 |
| | 2 | 9.09 ± 0.04 | 2.36 ± 0.55 |
| | 4 | 9.01 ± 0.44 | 3.31 ± 1.22 |
| | 6 | 9.39 ± 0.14 | 4.18 ± 0.27 |
| | 12 | 8.59 ± 0.15 | 4.53 ± 0.15 |
| | 60 | 8.63 ± 0.02 | 5.70 ± 1.00 |

Note that, the values of dissolution amount (n=3) in Table 7 are expressed as average±standard error.

For the result of Table 7 and FIG. 15, the pharmaceutical particles of Example 3 exhibited a sustained release property. A release rate of the water-soluble compound such as calcitonin was able to be controlled by enclosing the compound into a sustained release polymer using the liquid-column resonance method. It is presumed that this is because the calcitonin was uniformly dispersed in PLGA serving as the dispersing agent in the particles and the calcitonin enclosed in the PLGA was gradually released as the PLGA, which was a biodegradable polymer, was slowly hydrolyzed.

Test Example 8

The pharmaceutical particles of Example 3 were evaluated for an inhalation property in order to fully examine applicability of the pharmaceutical particles as transpulmonary administrated powder. The inhalation property was measured according to the method described in USP 2000 "Physical Tests and Determinations/Aerosols" and "Multistage Cascade Impactor Apparatus" under the following conditions.

-Measurement Condition-

Device: Andersen sampler (AN-200, available from SIBATA SCIENTIFIC TECHNOLOGY LTD.)
Pump flow rate: 28.3 L/min
Device used: JET HALLER (registered trademark) (available from Hitachi Automotive Systems, Ltd.)

The pharmaceutical particles of Example 3 were mixed with lactose (average particle diameter: 50 micrometers, RESPITOSE (registered trademark) (DMV Japan)) in an amount of 5 times as much as the amount of the pharmaceutical particles to obtain a powder preparation. About 30 mg of the thus-prepared powder preparation was filled into Japanese Pharmacopoeia No. 2 HPMC capsules. The resultant capsules were evaluated under an air stream at 28.3 L/min. The results are presented in Table 8 below and FIG. 16.

TABLE 8

| | | Distribution amount (%) |
|---|---|---|
| Residual CALCITONIN in capsules | | 20.1 |
| Stage No. | 0 | 3.6 |
| | 1 | 2.8 |
| | 2 | 5.0 |
| | 3 | 16.1 |
| | 4 | 5.8 |
| | 5 | 0.6 |
| | 6 | 0.1 |
| | 7 | 0.0 |

For the results of Table 8 and FIG. 16, it is demonstrated that the powder preparation was mainly distributed at Stages 2 to 4. Stages 2 to 7 in the Andersen cascade impactor are regions corresponding to from the bronchi to the alveoli in human. A percentage of particles distributed in these stages is defined as a fine particle fraction (FPF) value. The FPF value in the present Example is about 30%. Therefore, the preparation is believed to satisfactorily reach the alveoli, which is a major absorption site, and the bronchi. About 80% of the preparation was confirmed to be released from the capsules, indicating that the preparation had high flowability and high dispersibility. The pharmaceutical particles of Example 3 are characterized by extremely high spheroidicity and a narrow particle size distribution. It is presumed that, due to the characteristics, the particles are prevented from aggregating to each other and maintained good flowability and good dispersibility.

Test Example 9

A powder preparation prepared using the pharmaceutical particles of Example 3 was evaluated for a drug efficacy after transpulmonary administration. The powder preparation was prepared by mixing the pharmaceutical particles of Example 3 with lactose (average particle diameter: 50 micrometers, RESPITOSE, available from DMV Japan) in an amount of 5 times as much as the amount of the pharmaceutical particles. The powder preparation was transpulmonary administrated (40 micrograms/animal in terms of CALCITONIN) to male SD rats (from 6 to 8 week-old, available from Japan SLC, Inc.) and then a blood calcium concentration after the administration was measured over time. As a control group, a simply mixed powder was prepared by molding a mixture of CALCITONIN bulk powder and lactose. The CALCITONIN has a pharmacological action of decreasing the blood calcium concentration. Therefore, the blood calcium concentration was selected as an indicator for evaluating the drug efficacy of the pharmaceutical particles of Example 3. The pharmaceutical particles were transpulmonary administrated by inserting an inhaler (DP-4, available from Ina Research Inc.) into the airway under inhalation anesthesia with isoflurane and feeding compressed air. A time point immediately before the transpulmonary administration was defined as time zero. Change in blood calcium concentration over time was evaluated assuming that a blood calcium concentration at the time zero was 100%. The blood calcium concentration was measured using a METALLOASSAY calcium (Ca) measurement LS kit CPZIII (available from Metallogenics Co., Ltd.). The results are presented in Table 9 below and FIG. 17.

TABLE 9

| | Blood calcium concentration (%) | |
|---|---|---|
| Time (h) | CALCITONIN bulk powder | Pharmaceutical particles of Example 3 |
| 0 | 100 | 100 |
| 0.25 | 81.7 ± 11.6 | 69.6 ± 4.4 |
| 0.5 | 74.6 ± 0.9 | 62.5 ± 8.0 |
| 1 | 81.1 ± 10.1 | 63.1 ± 8.3 |
| 2 | 79.5 ± 7.1 | 61.3 ± 15.1 |
| 4 | 96.7 ± 5.1 | 64.6 ± 8.4 |
| 6 | 99.1 ± 12.6 | 66.0 ± 19.5 |
| 8 | 102.1 ± 15.9 | 61.4 ± 9.0 |
| 12 | 104.3 ± 13.8 | 54.8 ± 10.8 |
| 24 | 110.9 ± 5.5 | 81.1 ± 9.4 |

Note that, the values of blood calcium concentration (n=3 to 6) in Table 9 are expressed as average±standard error.

For the results of Table 9 and FIG. 17, the pharmaceutical particles prepared in Example 3 enhanced and kept the action of decreasing the blood calcium concentration of the CALCITONIN. It was confirmed that, as a result of the transpulmonary administration, the CALCITONIN reached the deep lung, was absorbed from the lung, entered systemic circulation, and developed a systemic action. The pharmaceutical particles prepared in Example 3 were believed to keep the pharmacological action longer than the CALCITONIN bulk powder because the pharmaceutical particles had the sustained release property which was confirmed in the evaluation test for dissolution property.

Test Example 10

The pharmaceutical particles of Example 1 and Comparative Example 8 were evaluated for powder properties. The evaluation results are presented in Table 10.

(Evaluation of Flowability)

An excitation-transfer flowability measurement device (available from dit Co., Ltd.) was used to evaluate flowability under evaluation conditions described below.

<Measurement Procedure>

(i) 1 g of a sample was weighed (conditioned under a measurement environment for 30 min).

(ii) An amplitude of the device was set to 7.5.

(iii) 1 g of the sample was mounted in the device and a measurement was started.

(iv) The flowability of powder was calculated as an average transfer amount according to the following expression:

Average transfer amount(mg/s)=450 mg/(Time to transfer 750 mg of powder−Time to transfer 300 mg of powder).

(Bulk Density)

A measuring cylinder method was used to measure a bulk density. Evaluation conditions are described below.

<Measurement Procedure>

(i) 1.5 g of a sample was weighed (conditioned under a measurement environment for 30 min).

(ii) The sample was gently poured into a 10 mL measuring cylinder.

(iii) After the measuring cylinder was left to stand for 10 min, a volume was read.

(iv) A bulk density was calculated from the volume and the weight: Bulk density (g/mL)=Sample weight (g)/Sample volume (mL).

(Evaluation of BET Specific Surface Area)

TRISTAR II 3020 (available from Micromeritics) was used to measure a BET specific surface area. Dehydration conditions and measurement conditions are described below.

Sample weight: 0.8 g

<Dehydration Condition>

Temperature: room temperature (25 degrees Celsius)

Pressure: 80 mTorr

Time: 5 hours

<Measurement Condition>

Measurement gas: nitrogen

Measurement times: 6

Calculation of parameter: multi-point method (Evaluation of True Specific Gravity)

ACCUPYC II 1340 (available from SHIMADZU CORPORATION) was used to evaluate a true specific gravity. Measurement conditions are described below.

<Measurement Condition>

Measurement cell volume: 11.2160 cm$^3$

Purge times: 10

Purge filling pressure: 19.5 psig

Measurement times: 5

Measurement filling pressure: 19.5 psig

Equilibrium pressure: 0.005 psig/min

Temperature: 23 degrees Celsius

Inert gas: Helium

TABLE 10

| | Flowability (mg/s) | Bulk density (g/mL) | BET specific surface area (m$^2$/g) | True specific gravity (g/cm$^3$) |
|---|---|---|---|---|
| Example 1 | 16.2 | 0.26 | 1.16 | 1.24 |
| Comparative Example 8 | 11.3 | 0.2 | 1.41 | 1.25 |

The pharmaceutical particles of Example 1 had a more excellent flowability than the pharmaceutical particles of Comparative Example 8. This is expected due to a uniform particle diameter and a spherical shape, which is believed to be reflected in the results of the BET specific surface area.

Aspects of the present invention are, for example, as follows.

<1> A method for producing particles, the method including:

applying vibration to a liquid including a physiologically active substance and included in a liquid-column resonance liquid-chamber to form a standing wave based on liquid column resonance, to thereby discharge the liquid from at least one discharging port, which is formed in an amplitude direction of the standing wave, to at least one region corresponding to at least one anti-node of the standing wave; and drying the liquid discharged, to thereby form particles.

<2> The method for producing particles according to <1>, wherein the physiologically active substance is a pharmaceutical compound.

<3> The method for producing particles according to <2>, wherein the pharmaceutical compound is at least one of cyclosporine and tranilast.

<4> The method for producing particles according to any one of <1> to <3>, wherein the particles have a particle size distribution (volume average particle diameter/number average particle diameter) of 1.00 or more but 1.50 or less.

<5> The method for producing particles according to any one of <1> to <4>, wherein the particles have the particle size distribution (volume average particle diameter/number average particle diameter) of 1.00 or more but 1.20 or less.

<6> The method for producing particles according to any one of <1> to <5>, wherein the particles have a volume average particle diameter of 1 micrometer or more but 10 micrometers or less.

<7> The method for producing particles according to any one of <1> to <6>, wherein the liquid further includes a dispersing agent.

<8> The method for producing particles according to <7>, wherein the dispersing agent is cellulose.

<9> The method for producing particles according to <8>, wherein the cellulose is hydroxypropylcellulose.

<10> The method for producing particles according to <9>, wherein the hydroxypropylcellulose has the weight average molecular weight is 15,000 or more but 400,000 or less.

<11> The method for producing particles according to <9> or <10>, wherein a 2% by mass aqueous solution of the hydroxypropylcellulose (at 20 degrees Celsius) has a viscosity of 2.0 mPa·s or more but 4,000 mPa·s or less.

<12> The method for producing particles according to any one of <1> to <11>, wherein the liquid further includes a solvent.

<13> The method for producing particles according to <12>, wherein the solvent is at least one selected from the group consisting of dichloromethane, 1,4-dioxane, methanol, and ethanol.

<14> The method for producing particles according to any one of <1> to <13>, wherein the liquid has the viscosity of 5.0 mPa·s or more but 15.0 mPa·s or less.

<15> The method for producing particles according to any one of <1> to <14>, wherein the liquid has a surface tension of 10 mN/m or more but 60 mN/m or less.

<16> The method for producing particles according to any one of <1> to <15>, wherein the particles have the number average particle diameter of 1 micrometer or more but 10 micrometers or less.

<17> The method for producing particles according to any one of <1> to <16>, wherein the particles have the particle size distribution (volume average particle diameter/number average particle diameter) of 1.00 or more but 1.10 or less.

<18> The method for producing particles according to any one of <1> to <17>, wherein the vibration to be applied to form the standing wave has a frequency of 150 kHz or more.

<19> The method for producing particles according to any one of <1> to <18>, wherein the vibration has the frequency of 300 kHz or more but 500 kHz or less.

<20> The method for producing particles according to any one of <1> to <19>, wherein the discharging ports have a diameter of 1 micrometer or more but 40 micrometers or less.

The method for producing particles according to any one of <1> to <20> is capable of solving the above existing problems and achieving the object of the present invention.

REFERENCE SIGNS LIST

14: liquid
18: liquid-column resonance liquid-chamber
19: discharging port

The invention claimed is:

1. A method for producing particles containing a physiologically active substance, the method comprising:
   (a) controlling a vibration generating section of a liquid discharging apparatus to apply vibration to a liquid (i) including the physiologically active substance and (ii) included in a liquid-column resonance liquid-chamber, to form, by liquid column resonance of the liquid in the liquid-column resonance liquid-chamber, a standing wave having at least one anti-node of maximum displacement in a direction of amplitude, to thereby discharge the liquid from at least one discharging port in a liquid discharge direction, which is parallel to said direction of amplitude, to at least one region corresponding to at least one anti-node of the standing wave; and
   (b) drying the liquid discharged, to thereby form particles, the physiologically active substance contained in the particles including a pharmaceutical compound, and the pharmaceutical compound constituting 5% by mass or more but 95% by mass or less relative to a total mass of the particles.

2. The method for producing particles according to claim 1, wherein the pharmaceutical compound constitutes 5% by mass or more but 50% by mass or less relative to the total mass of the particles.

3. The method for producing particles according to claim 1, wherein the liquid to which the vibration is applied in (a) further includes a dispersing agent to disperse the physiologically active substance, and the dispersing agent includes at least one selected from the group consisting of lipids, saccharides, cyclodextrins, amino acids, and organic acids.

4. The method for producing particles according to claim 1, wherein the liquid to which the vibration is applied in (a) further includes a polymeric dispersing agent to disperse the physiologically active substance.

5. The method for producing particles according to claim 4, wherein the polymeric dispersing agent to disperse the physiologically active substance includes one or more water-soluble celluloses.

6. A method for producing particles containing a physiologically active substance, the method comprising:

(a) controlling a vibration generating section of a liquid discharging apparatus to apply vibration to a liquid (i) including the physiologically active substance and a dispersing agent to disperse the physiologically active substance, and (ii) included in a liquid-column resonance liquid-chamber, to form, by liquid column resonance of the liquid in the liquid-column resonance liquid-chamber, a standing wave having at least one anti-node of maximum displacement in a direction of amplitude, to thereby discharge the liquid from at least one discharging port in a liquid discharge direction, which is parallel to said direction of amplitude, to at least one region corresponding to at least one anti-node of the standing wave; and (b) drying the liquid discharged in (a), to thereby form particles containing the physiologically active substance.

7. The method for producing particles according to claim 6, wherein the physiologically active substance is a pharmaceutical compound.

8. The method for producing particles according to claim 6, wherein the particles have a particle size distribution (volume average particle diameter/number average particle diameter) of 1.00 or more but 1.50 or less.

9. The method for producing particles according to claim 6, wherein the particles have the particle size distribution (volume average particle diameter/number average particle diameter) of 1.00 or more but 1.20 or less.

10. The method for producing particles according to claim 6, wherein the particles have a volume average particle diameter of 1 micrometer or more but 10 micrometers or less.

11. The method for producing particles according to claim 6, wherein the dispersing agent constitutes 5% by mass or more but 95% by mass or less relative to a total mass of the particles.

12. The method for producing particles according to claim 6, wherein the dispersing agent constitutes 50% by mass or more but 95% by mass or less relative to a total mass of the particles.

13. The method for producing particles according to claim 6, wherein the dispersing agent in the liquid applied in (a) includes a polymeric dispersing agent to disperse the physiologically active substance.

14. The method for producing particles according to claim 13, wherein the polymeric dispersing agent, in the liquid applied in (a), includes one or more water-soluble celluloses.

15. The method for producing particles according to claim 6, wherein the dispersing agent in the liquid applied in (a) includes at least one selected from the group consisting of lipids, saccharides, cyclodextrins, amino acids, and organic acids.

16. The method for producing particles according to claim 6, wherein the physiologically active substance is a pharmaceutical compound, and the pharmaceutical compound constitutes 5% by mass or more but 95% by mass or less relative to a total mass of the particles.

17. The method for producing particles according to claim 6, wherein the physiologically active substance is a pharmaceutical compound, and the pharmaceutical compound constitutes 5% by mass or more but 50% by mass or less relative to a total mass of the particles.

* * * * *